United States Patent
Conroy et al.

(10) Patent No.: US 9,631,152 B2
(45) Date of Patent: *Apr. 25, 2017

(54) FUEL MARKERS AND METHODS OF PRODUCING AND USING SAME

(71) Applicant: Authentix, Inc., Addison, TX (US)

(72) Inventors: Jeffrey L. Conroy, Allen, TX (US); Philip B. Forshee, McKinney, TX (US); John-Christopher Boyer, Dallas, TX (US)

(73) Assignee: Authentix, Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/806,389

(22) Filed: Jul. 22, 2015

(65) Prior Publication Data

US 2016/0272906 A1    Sep. 22, 2016

Related U.S. Application Data

(60) Provisional application No. 62/194,088, filed on Jul. 17, 2015, provisional application No. 62/136,068, filed on Mar. 20, 2015.

(51) Int. Cl.
*C10L 1/24* (2006.01)
*G01N 33/22* (2006.01)
(Continued)

(52) U.S. Cl.
CPC ........ *C10L 1/2406* (2013.01); *C07C 43/2055* (2013.01); *C07C 43/21* (2013.01);
(Continued)

(58) Field of Classification Search
CPC .................................................. C10L 2230/16
(Continued)

(56) References Cited

U.S. PATENT DOCUMENTS 5,012,052 A    4/1991    Hayes
5,981,283 A   11/1999   Anderson, II et al.
(Continued)

FOREIGN PATENT DOCUMENTS

AU    2012201141 A1    3/2012
EP       0624250 B1    4/2003
(Continued)

OTHER PUBLICATIONS

Office Action dated Nov. 10, 2015 (30 pages), U.S. Appl. No. 14/806,404, filed Jul. 22, 2015.
(Continued)

*Primary Examiner* — Ellen McAvoy
(74) *Attorney, Agent, or Firm* — Conley Rose, P.C.; Rodney B. Carroll

(57) ABSTRACT

A method of forming a composition comprising contacting a fuel and at least one compound of Formula I:

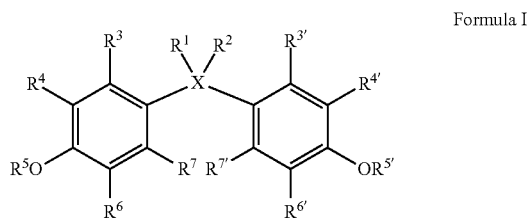

Formula I wherein X is carbon, oxygen, or sulfur; $R^1$ and $R^2$ each independently are hydrogen, a $C_1$ to $C_{20}$ alkyl, or a $C_6$ to $C_{10}$ aryl; $R^3$ and $R^{3'}$ each independently are hydrogen or a $C_1$ to $C_4$ alkyl; $R^4$ and $R^{4'}$ each independently are hydrogen, a $C_1$ to $C_4$ alkyl, a $C_4$ to $C_{10}$ cycloalkyl, or a $C_6$ to $C_{10}$ aryl; $R^5$ and $R^{5'}$ each independently are a $C_4$ to $C_{10}$ alkyl; $R^6$ and $R^{6'}$ each
(Continued)

independently are hydrogen or a $C_1$ to $C_6$ alkyl; and $R^7$ and $R^{7'}$ each independently are hydrogen or $C_1$ to $C_4$ alkyl; and wherein the compound of Formula I when subjected to GC-MS using electron ionization at greater than 70 eV produces at least one ion having a mass-to-charge ratio of 300 to 600.

21 Claims, 3 Drawing Sheets

(51) Int. Cl.
| | |
|---|---|
| *C07C 323/20* | (2006.01) |
| *C07C 43/263* | (2006.01) |
| *G01N 30/72* | (2006.01) |
| *C07C 43/205* | (2006.01) |
| *C07C 43/21* | (2006.01) |
| *C07C 43/275* | (2006.01) |
| *C07C 321/30* | (2006.01) |
| *C10L 1/185* | (2006.01) |
| *C10L 10/00* | (2006.01) |
| *G01N 21/65* | (2006.01) |
| *G01N 24/08* | (2006.01) |
| *G01N 30/02* | (2006.01) |

(52) U.S. Cl.
CPC .......... *C07C 43/263* (2013.01); *C07C 43/275* (2013.01); *C07C 321/30* (2013.01); *C07C 323/20* (2013.01); *C10L 1/1852* (2013.01); *C10L 1/2412* (2013.01); *C10L 10/00* (2013.01); *G01N 21/65* (2013.01); *G01N 30/7206* (2013.01); *G01N 33/22* (2013.01); *C07B 2200/05* (2013.01); *C07C 2101/14* (2013.01); *C10L 2200/0263* (2013.01); *C10L 2230/16* (2013.01); *G01N 24/08* (2013.01); *G01N 2030/025* (2013.01)

(58) Field of Classification Search
USPC .................................................. 44/435, 447
See application file for complete search history.

(56) References Cited

U.S. PATENT DOCUMENTS

| | | | |
|---|---|---|---|
| 6,514,917 | B1 | 2/2003 | Smith et al. |
| 8,574,323 | B2* | 11/2013 | Green ..................... C10L 1/003 44/447 |
| 8,592,213 | B2 | 11/2013 | Wilkinson et al. |
| 8,961,624 | B2* | 2/2015 | Green ..................... C10L 1/003 436/56 |
| 9,005,315 | B2* | 4/2015 | Green .................. C10L 1/1852 44/440 |
| 2006/0173222 | A1 | 8/2006 | Dhalla et al. |
| 2010/0304492 | A1 | 12/2010 | Melechco Carvalho et al. |
| 2011/0207039 | A1 | 8/2011 | Yamada et al. |
| 2014/0120626 | A1* | 5/2014 | Stubbs ..................... C10L 1/003 436/56 |
| 2014/0134746 | A1* | 5/2014 | Green ..................... C10L 1/003 436/127 |
| 2015/0307795 | A1* | 10/2015 | Green ..................... C10L 1/003 44/442 |
| 2015/0344796 | A1* | 12/2015 | Swedo ..................... C10L 1/003 44/440 |

FOREIGN PATENT DOCUMENTS

| | | |
|---|---|---|
| GB | 2484826 A | 4/2012 |
| WO | 9315398 A1 | 8/1993 |
| WO | 2014083156 A2 | 6/2014 |
| WO | 2014083156 A3 | 6/2014 |
| WO | 2014088898 A1 | 6/2014 |

OTHER PUBLICATIONS

Foreign communication from a related counterpart application—Extended European Search Report dated Feb. 29, 2016, EP 15197644.6, 6 pages.
Filing receipt and specification for provisional patent application entitled "Fuel Markers and Methods of Producing and Using Same," by Jeffrey L. Conroy, et al., filed on Mar. 20, 2015 as U.S. Appl. No. 62/136,068.
Filing receipt and specification for provisional patent application entitled "Fuel Markers and Methods of Producing and Using Same," by Jeffrey L. Conroy, et al., filed on Jul. 17, 2015 as U.S. Appl. No. 62/194,088.
Filing receipt and specification for patent application entitled "Fuel Markers and Methods of Producing and Using Same," by Jeffrey L. Conroy, et al., filed on Jul. 22, 2015 as U.S. Appl. No. 14/806,381.
Filing receipt and specification for patent application entitled "Fuel Markers and Methods of Producing and Using Same," by Jeffrey L. Conroy, et al., filed on Jul. 22, 2015 as U.S. Appl. No. 14/806,404.
Advisory Action dated Feb. 9, 2016 (3 pages), U.S. Appl. No. 14/806,404, filed Jul. 22, 2015.
Filing receipt and specification for patent application entitled "Fuel Markers and Methods of Producing and Using Same," by Jeffrey L. Conroy, et al., filed on Feb. 23, 2016 as U.S. Appl. No. 15/051,196.
Office Action (Final) dated Dec. 11, 2015 (28 pages), U.S. Appl. No. 14/806,404, filed Jul. 22, 2015.
Notice of Allowance dated Mar. 10, 2016 (10 pages), U.S. Appl. No. 14/806,404, filed Jul. 22, 2015.
Foreign communication from a related counterpart application—Partial European Search Report dated Aug. 9, 2016, EP 16158792.8 filed on Mar. 4, 2016, 5 pages.
Office Action (Final) dated Jun. 7, 2016 (16 pages), U.S. Appl. No. 15/051,196, filed Feb. 23, 2016.
Alisova E. V., et al., "Simultaneous reaction of acetyl chloride with cyclohexene and phenetole in the presence of aluminum chloride," Zhurnal Organicheskoi Khimii,1985, pp. 1066-1068, vol. 21, No. 5, XP-002721069, 1 page abstract.
Foreign communication from a related counterpart application—Extended European Search Report dated Nov. 11, 2016, EP 16158792.8 filed on Mar. 4, 2016, 9 pages.
Office Action dated Oct. 6, 2016 (36 pages), U.S. Appl. No. 14/806,381, filed Jul. 22, 2015.
Office Action dated Mar. 31, 2016 (21 pages), U.S. Appl. No. 15/051,196, filed Feb. 23, 2016.

* cited by examiner

FUEL MARKERS AND METHODS OF PRODUCING AND USING SAME

CROSS-REFERENCE TO RELATED APPLICATIONS

The present application is a non-provisional of and claims priority to U.S. Provisional Application Nos. 62/136,068 filed Mar. 20, 2015 and 62/194,088, filed on Jul. 17, 2015 and both entitled "Fuel Markers and Methods of Producing and Using Same," each of which is incorporated by reference herein in its entirety.

TECHNICAL FIELD

The present disclosure relates to fuel compositions, more specifically marked fuel compositions and methods of producing and using same.

BACKGROUND

Fuels represent a crucial energy supply and an important revenue source. Based on their provenience and quality (e.g., different grades or types of fuel), fuels can be differentially priced, such as taxed fuel and subsidized fuel or tax-free fuel; kerosene; diesel fuel; low-octane gasoline; high-octane gasoline; etc. Fuels can be differentially priced for a variety of reasons. In some countries, liquid fuel, such as diesel fuel, kerosene, and liquefied petroleum gas, is subsidized or sold below market rates to provide more widespread access to resources. Fuel can also be subsidized to protect certain industry sectors, such as public transportation.

Fuel adulteration is a clandestine and profit-oriented operation that is conducted for financial gain, which operation is detrimental to the rightful owner. Sometimes, fuels can be adulterated by mixing together fuels from different sources to obscure the origin of one or more of the fuels. Other times, adulterated fuels can be obtained by mixing higher priced fuel with lower priced fuel (e.g., lower grade fuel) or adulterants such as solvents. In some cases, subsidized fuel can be purchased and then re-sold, sometimes illegally, at a higher price. For example, subsidized fuel can be purchased and then mixed with other fuel to disguise the origin of the subsidized fuel.

Fuel markers can be added to fuels to establish ownership and/or origin of fuel. However, some markers placed in fuel for authentication can sometimes be at least partially removed to disguise the origin of the fuel. While some methods have employed the use of deuterated structures as fuel markers, such methods do not use of deuterated isotopologues to improve the accuracy of analysis.

Fuel adulteration can be assessed by determining the presence and concentration of fuel markers in a fuel sample via a variety of analytical techniques, such as gas chromatography (GC), mass spectrometry (MS), etc. Fuel markers can interact with their immediate environment (e.g., matrix), such as fuel, solvent, masking agents, etc., surrounding the marker, and the effect of the matrix can hinder the analysis of a fuel sample for determining whether a fuel is adulterated or not. While most prominently reported in trace level analysis of pesticide residues, matrix effects have been attributed to matrix components which cannot be efficiently separated from analytes of interest via a specified sample preparation methodology.

There have been a variety of approaches to mitigate matrix effects, such as for example pulsed inlet conditions, matrix matched standards, inclusion of analyte protectants in analytical samples, etc. While these approaches could improve detectability of target analytes (e.g., fuel markers) in some instances, their application to routine analyses proves rather complicated from a practical point of view. These approaches are usually neither generally applicable to a wide variety of chemical classes of fuel marker, nor desirable as they would add significant cost, time and complexity to the analysis.

Another approach to mitigate matrix effects can employ "matrix matched standards," where standards can be prepared from the same matrix to be analyzed. While this approach can represent a way to reliably correct for matrix effects, a diverse matrix in combination with the lack of a priori knowledge of what problematic components are present in the matrix can prevent this approach from being an effective solution.

Yet another approach to mitigate matrix effects can employ analyte spiking (also known as "method of standard addition"), which entails adding known amounts of a standard to one or more aliquots of an unknown sample. This approach can generate a standard curve where the y-intercept of the linear regression fit of the collected data represents the endogenous concentration of the analyte (e.g., fuel marker) in the sample. While theoretically this approach could work, practically it entails too high of a cost in terms of time (requires 2-4 additional analyses per unknown sample) and the analysis of the data can be considered too complex for the practical purpose of fuel authentication.

Existing analytical approaches to determine fuel adulteration and mitigate matrix effects all have significant limitations that preclude their utility in fuel authentication. Thus, there is an ongoing need to develop and/or improve fuel markers and methods for detecting these markers.

BRIEF SUMMARY

Disclosed herein is a method of forming a composition comprising contacting (a) a fuel and (b) at least one compound characterized by Formula I:

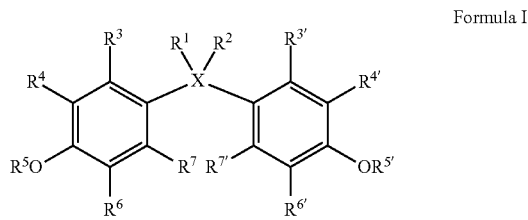

Formula I wherein X can be carbon (C), oxygen (O), or sulfur (S); $R^1$ and $R^2$ can each independently be hydrogen, a $C_1$ to $C_{20}$ alkyl group, or a $C_6$ to $C_{10}$ aryl group; $R^3$ and $R^{3'}$ can each independently be hydrogen or a $C_1$ to $C_4$ alkyl group; $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group; $R^5$ and $R^{5'}$ can each independently be a $C_4$ to $C_{10}$ alkyl group; $R^6$ and $R^{6'}$ can each independently be hydrogen or a $C_1$ to $C_6$ alkyl group; and $R^7$ and $R^{7'}$ can each independently be hydrogen or a $C_1$ to $C_4$ alkyl group; and wherein the compound characterized by Formula I when subjected to gas chromatography-mass spectrometry (GC-MS) using electron ionization produces at least one ion having a mass-to-charge ratio of from about 300 to about 600 at an ionization energy of equal to or greater than about 70 eV.

BRIEF DESCRIPTION OF THE DRAWINGS

For a more complete understanding of the present disclosure and advantages thereof, reference will now be made to the accompanying drawings/figures in which.

DETAILED DESCRIPTION

Figure 1:
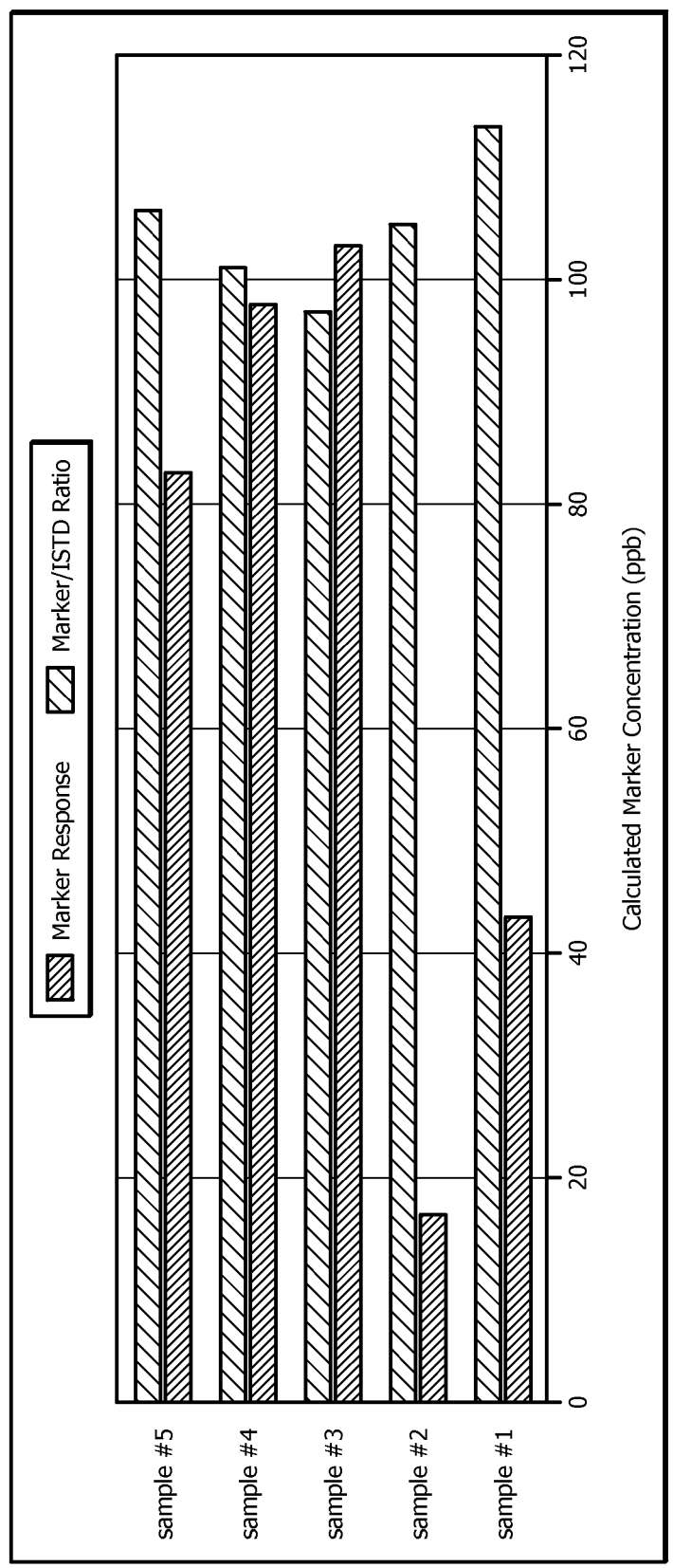
FIG. 1 displays a graph of calculated fuel marker concentrations for several diesel fuel samples.

Disclosed herein are marked fuel compositions and methods of determining adulteration of same. In an embodiment, a marked fuel composition can comprise a fuel and a fuel marker, wherein the fuel marker comprises at least one compound characterized by Formula I:

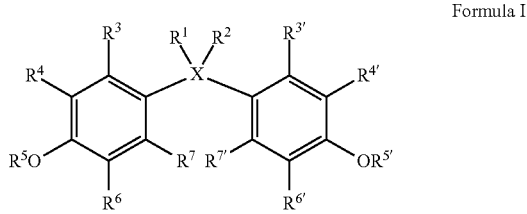

Formula I wherein X can be carbon (C), oxygen (O), or sulfur (S); $R^1$ and $R^2$ can each independently be hydrogen, a $C_1$ to $C_{20}$ alkyl group, or a $C_6$ to $C_{10}$ aryl group; $R^3$ and $R^{3'}$ can each independently be hydrogen or a $C_1$ to $C_4$ alkyl group; $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group; $R^5$ and $R^{5'}$ can each independently be a $C_4$ to $C_{10}$ alkyl group; $R^6$ and $R^{6'}$ can each independently be hydrogen or a $C_1$ to $C_6$ alkyl group; and $R^7$ and $R^{7'}$ can each independently be hydrogen or a $C_1$ to $C_4$ alkyl group. The compound characterized by Formula I can be further subjected to gas chromatography-mass spectrometry (GC-MS) using electron ionization, wherein the compound characterized by Formula I produces at least one ion having a mass-to-charge ratio of from about 300 to about 600 at an ionization energy of equal to or greater than about 70 eV.

In an embodiment, a method of the present disclosure can comprise contacting (a) a fuel and (b) at least one compound characterized by Formula I to yield a marked fuel composition. In an embodiment, the method can further comprise subjecting the marked fuel composition to an analytical technique for determining adulteration of the fuel. As used herein, "adulteration" of a fuel refers to altering, mixing, diluting, laundering, etc., of the fuel. In some cases, a fuel (e.g., a fuel taxed at a higher rate) can be combined (e.g., illegally) "as is" with another fuel (e.g., an untaxed fuel or fuel taxed at a lower rate) or solvent to form an adulterated (e.g., altered, mixed, diluted, laundered, etc.) fuel. For example, a fuel can be mixed with one or more other fuels, solvents, and the like, or combinations thereof. If undetected, the adulterated fuel can be sold, sometimes illegally, at the price of the fuel taxed at the higher rate to yield a profit. In some instances, the adulterated fuel can be potentially hazardous for the user, such as for example when a hazardous solvent is used for adulterating the fuel. In other instances, the fuel can be treated or "laundered" in an attempt to remove identifying features such as markers from the fuel (e.g., to disguise the origin of the fuel, the amount of tax paid on the fuel, etc.) before the fuel is mixed with another fuel to form an adulterated fuel.

In an embodiment, a method of determining adulteration of a fuel comprises subjecting to an analytical technique a marked fuel mixture comprising (a) a fuel; (b) a compound characterized by Formula I; and (c) a heavy compound, wherein the heavy compound comprises a compound of Formula I having at least one atom replaced with an isotope tag. Generally, an isotope tag refers to an isotope of a particular atom that replaced such particular atom in a molecule, as will be described in more detail later herein.

In an embodiment, a method of determining adulteration of a fuel further comprises (i) acquiring a fuel sample; (ii) adding a known amount of the heavy compound to the fuel sample to yield a marked fuel mixture; (iii) subjecting the marked fuel mixture to the analytical technique to record an analytical signal for the compound characterized by Formula I and an analytical signal for the heavy compound; (iv) comparing the analytical signal for the known amount of heavy compound to the analytical signal for the compound characterized by Formula I; (v) determining a ratio of an amount of the compound characterized by Formula I to the known amount of the heavy compound in the marked fuel mixture; and (vi) calculating the amount of the compound characterized by Formula I in the marked fuel mixture. As will be appreciated by one of skill in the art, and with the help of this disclosure, "amount" can refer to any suitable ways of expressing how much compound (e.g., fuel marker, heavy compound, etc.) is present in a composition (e.g., marked fuel composition, marked fuel mixture, etc.), such as for example concentration, molarity, molality, percent composition, mole fraction, weight fraction, parts per million (ppm), parts per billion (ppb), etc. For purposes of the disclosure herein, ppb and ppm are expressed as mass/mass (m/m), unless otherwise specified.

In an embodiment, a method of determining adulteration of a fuel comprises (i) contacting a fuel sample with a heavy compound to form a marked fuel mixture, wherein the fuel sample comprises a fuel and a compound characterized by Formula I, and wherein the heavy compound comprises the compound of Formula I having at least one atom replaced with an isotope tag; (ii) subjecting the marked fuel mixture to solid phase extraction (SPE) to yield a marked fuel mixture fraction, wherein at least a portion of the compound characterized by Formula I and at least a portion of the heavy compound elute together in the marked fuel mixture fraction; and (iii) subjecting to an analytical technique the marked fuel mixture fraction to determine fuel adulteration. In such an embodiment, the analytical technique comprises GC-MS using electron ionization, wherein the compound characterized by Formula I can produce at least one ion having a mass-to-charge ratio of from about 300 to about 600 at an ionization energy of equal to or greater than about 70 eV.

While the present disclosure will be discussed in detail in the context of a method of determining adulteration of a fuel, it should be understood that such method or any steps thereof can be applied in a method of authenticating any other suitable liquid mixture. The liquid mixture can comprise any liquid mixture compatible with the disclosed methods and materials. As used herein, "authenticating" of a fuel or any other suitable liquid mixture refers to determining whether the fuel or any other suitable liquid mixture has been adulterated. Authenticating of a fuel or any other suitable liquid mixture can comprise detecting the presence and amount (e.g., concentration) of markers (e.g., fuel markers) in the fuel or any other suitable liquid mixture, as will be described in more detail later herein.

In an embodiment, the marked fuel composition can comprise a fuel. Generally, a fuel is a material or substance that stores potential energy that can be released as useful energy (e.g., heat or thermal energy, mechanical energy, kinetic energy, etc.) when the material undergoes a chemical reaction (e.g., combustion).

In an embodiment, the fuel comprises a naturally-occurring material. Alternatively, the fuel comprises a synthetic material. Alternatively, the fuel comprises a mixture of a naturally-occurring and a synthetic material. Nonlimiting examples of fuels suitable for use in the present disclosure include gasoline, diesel, jet fuel, kerosene, non-petroleum derived fuels, alcohol fuels, ethanol, methanol, propanol, butanol, biodiesel, maritime fuels, and the like, or combinations thereof.

In an embodiment, the marked fuel composition can comprise a fuel marker. In an embodiment, the fuel maker can comprise at least one compound characterized by Formula I:

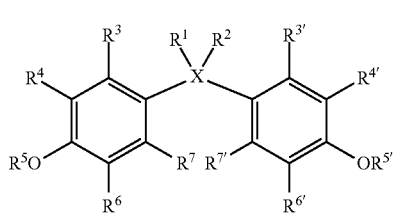

Formula I wherein X can be carbon (C), oxygen (O), or sulfur (S); $R^1$ and $R^2$ can each independently be hydrogen, a $C_1$ to $C_{20}$ alkyl group, or a $C_6$ to $C_{10}$ aryl group; $R^3$ and $R^{3'}$ can each independently be hydrogen or a $C_1$ to $C_4$ alkyl group; $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group; $R^5$ and $R^{5'}$ can each independently be a $C_4$ to $C_{10}$ alkyl group; $R^6$ and $R^{6'}$ can each independently be hydrogen or a $C_1$ to $C_6$ alkyl group; and $R^7$ and $R^{7'}$ can each independently be hydrogen or a $C_1$ to $C_4$ alkyl group. The compound characterized by Formula I can be further subjected to GC-MS using electron ionization, wherein the compound characterized by Formula I produces at least one ion having a mass-to-charge ratio of from about 300 to about 600 at an ionization energy of equal to or greater than about 70 eV, as will be described in more detail later herein. In an embodiment, the marked fuel composition can comprise at least two compounds characterized by Formula I.

In an embodiment of the compound characterized by Formula I, X is O or S. In such an embodiment, $R^1$ and $R^2$ can be lone non-bonding electron pairs. Generally, a lone non-bonding electron pair is a pair of electrons (e.g., a valence set of two electrons) that is not bonding or shared with another atom—as opposed to bonding electron pairs that are shared between different atoms, as they form bonds (e.g., covalent bonds) between such atoms.

In an embodiment of the compound characterized by Formula I, X is O. In such an embodiment, the compound characterized by Formula I can have Structure A:

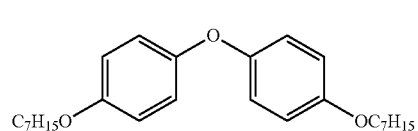

Structure A

In an embodiment of the compound characterized by Formula I, X is S. In such an embodiment, the compound characterized by Formula I can have any of Structure B, Structure C, Structure D, Structure E, or Structure F:

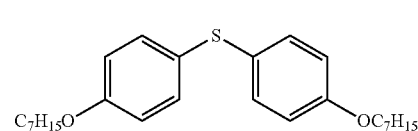

Structure B

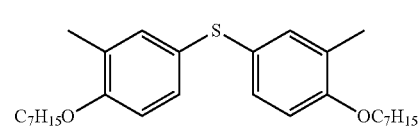

Structure C

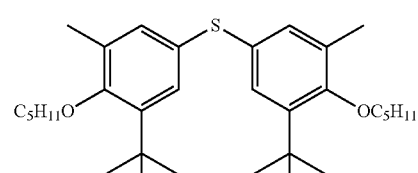

Structure D

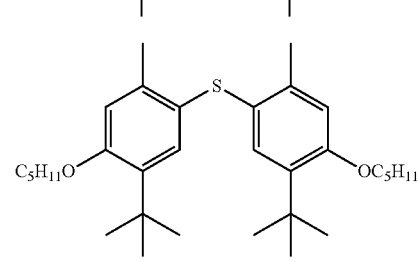

Structure E

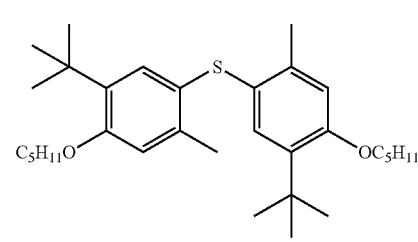

Structure F

In an embodiment of the compound characterized by Formula I, X is C. In such an embodiment, $R^1$ and $R^2$ can each independently be hydrogen, a $C_1$ to $C_{20}$ alkyl group, or a $C_6$ to $C_{10}$ aryl group.

In an embodiment of the compound characterized by Formula I, X is C, and $R^1$ and $R^2$ can each independently be a $C_1$ to $C_{20}$ alkyl group, alternatively a $C_1$ to $C_{10}$ alkyl group, alternatively a $C_1$ to $C_7$ alkyl group, or alternatively a $C_1$ to $C_4$ alkyl group. As used herein, the term "alkyl group" is a general term that refers to any univalent group derived from an alkane by removal of a hydrogen atom from any carbon atom of the alkane. Further, as used herein, the term "alkyl groups" can refer to primary alkyl groups, secondary alkyl groups (sec-alkyl groups), or tertiary alkyl groups (tert-alkyl groups or t-alkyl groups). Alkanes are acyclic branched or unbranched hydrocarbons having the general formula $C_nH_{2n+2}$ and consist entirely of hydrogen atoms and saturated carbon atoms. For purposes of the disclosure herein, the term "alkyl group" refers to any alkyl group, including without limitation primary alkyl groups, sec-alkyl groups, tert-alkyl groups, n-alkyl groups, iso-alkyl groups, substituted alkyl groups, unsubstituted or non-substituted alkyl groups, and the like, or combinations thereof. For example, the term "butyl group" refers to a n-butyl group, an iso-butyl group, a sec-butyl group, a tert-butyl group, or combinations thereof. Generally, a "substituted organic group" (e.g., substituted alkyl group, substituted cycloalkyl group, substituted aryl group, etc.) refers to an organic group wherein a hydrogen atom has been substituted with an atom or group of atoms, e.g., a substituent. For purposes of the disclosure herein, a $C_x$ to $C_y$ organic group (e.g., an alkyl group, a cycloalkyl group, an aryl group, etc.) includes groups represented by all integers between x and y, including x and y. For example, a $C_1$ to $C_{10}$ organic group includes $C_1$, $C_2$, $C_3$, $C_4$, $C_5$, $C_6$, $C_7$, $C_8$, $C_9$, and $C_{10}$ organic groups. Further, for example, a $C_6$ to $C_{12}$ organic group includes $C_6$, $C_7$, $C_8$, $C_9$, $C_{10}$, $C_{11}$ and $C_{12}$ organic groups.

In an embodiment of the compound characterized by Formula I, X is C, and $R^1$ and $R^2$ can each independently be selected from the group consisting of a methyl group, an ethyl group, a n-propyl group, an iso-propyl group, a n-butyl group, an iso-butyl group, a sec-butyl group, a tert-butyl group, a pentyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group and a nonadecyl group.

In an embodiment of the compound characterized by Formula I, X is C, and $R^1$ and $R^2$ can each independently be selected from the group consisting of a methyl group, an ethyl group, a n-propyl group, an iso-propyl group, a n-butyl group, an iso-butyl group, a sec-butyl group, a tert-butyl group and a heptyl group.

In an embodiment of the compound characterized by Formula I, X is C, and $R^1$ and $R^2$ can each be a methyl group.

In an embodiment of the compound characterized by Formula I, X is C, and $R^1$ and $R^2$ can each independently be a $C_6$ to $C_{10}$ aryl group, alternatively a $C_6$ to $C_8$ aryl group, alternatively a $C_6$ aryl group, alternatively a $C_7$ aryl group, or alternatively a $C_8$ aryl group. As used herein, the term "aryl group" is a general term that refers to any aromatic group derived from an arene by removal of a hydrogen atom from any carbon atom of an aromatic ring. Generally, arenes (or aromatic hydrocarbons) are hydrocarbons with alternating double bonds and single bonds between carbon atoms, wherein the carbon atoms form rings, and can be monocyclic arenes (e.g., benzene, toluene, o-xylene, m-xylene, p-xylene, biphenyl, diphenylmethane, etc.), which can contain one or more aromatic rings, wherein the rings are not fused to each other; or polycyclic arenes (e.g., naphthalene, anthracene, etc.), which can contain two or more aromatic rings, wherein at least two of the rings are fused to each other. Except for phenyl, which is derived by removal of a hydrogen atom from a carbon atom of a benzene ring, all other aryl groups are position dependent, with respect to the already existing substituents on the aromatic ring from which the hydrogen is removed to create such aryl group. For example, a tolyl group can be obtained by removing one hydrogen atom from a carbon atom of the aromatic ring of toluene, wherein such tolyl group can be o-tolyl, m-tolyl, or p-tolyl, based on whether the hydrogen was removed from a carbon that was positioned in ortho, metha, or para, respectively, with respect to the methyl group. For purposes of the disclosure herein, the term "aryl group" refers to any aryl group, including without limitation any isomers, such as ortho, meta, para isomers, a substituted aryl group, a unsubstituted aryl group, and the like, or combinations thereof. For example, the term "tolyl group" refers to o-tolyl group, m-tolyl group, p-tolyl group, or combinations thereof.

In an embodiment of the compound characterized by Formula I, X is C, and $R^1$ and $R^2$ can each independently be hydrogen, a $C_1$ to $C_{10}$ alkyl group, or a $C_6$ to $C_{10}$ aryl group, wherein the $C_6$ to $C_{10}$ aryl group can comprise a phenyl group, a substituted phenyl group, a tolyl group, a substituted tolyl group, a xylyl group, or a substituted xylyl group.

In an embodiment of the compound characterized by Formula I, X is C. In such an embodiment, the compound characterized by Formula I can have any of Structures G-O:

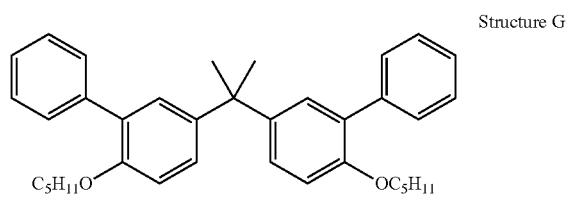

Structure G

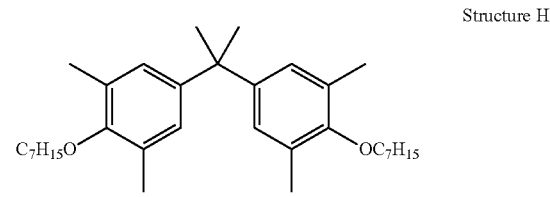

Structure H

Structure I

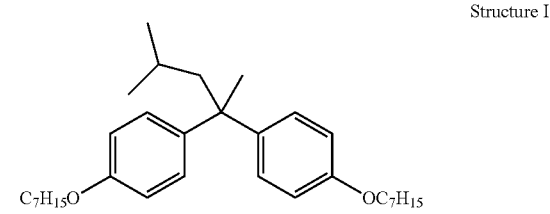

Structure J

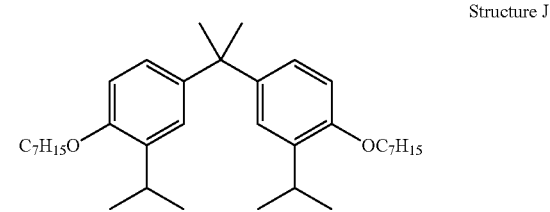

Structure K

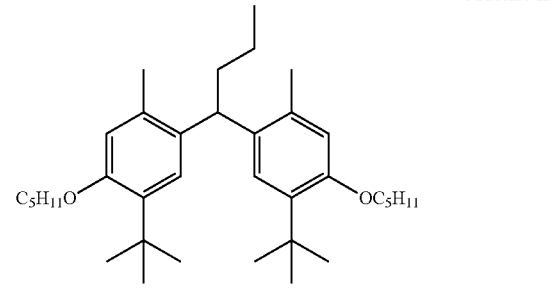

-continued

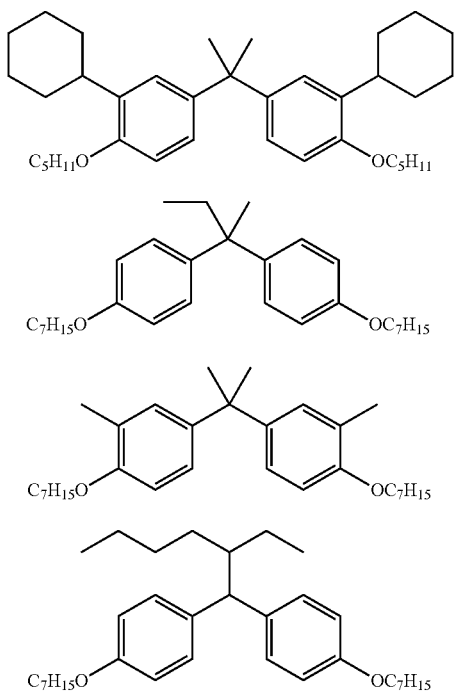

Structure L

Structure M

Structure N

Structure O

In an embodiment of the compound characterized by Formula I, X is C, and $R^1$ and $R^2$ can each independently be a $C_1$ to $C_4$ alkyl group, or a $C_6$ to $C_{10}$ aryl group; wherein the $C_6$ to $C_{10}$ aryl group can comprise a phenyl group, a substituted phenyl group, a tolyl group, a substituted tolyl group, a xylyl group, or a substituted xylyl group.

In an embodiment of the compound characterized by Formula I, X is C, and $R^1$ and $R^2$ can each independently be selected from the group consisting of a methyl group, an ethyl group, a n-propyl group, an iso-propyl group, a n-butyl group, an iso-butyl group, a sec-butyl group, a tert-butyl group, a pentyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group and a nonadecyl group. In such an embodiment, the compound characterized by Formula I can have any of Structure G, Structure H, Structure I, Structure J, Structure K, Structure L, Structure M, Structure N, or Structure O.

In an embodiment of the compound characterized by Formula I, X is C. In such an embodiment, the compound characterized by Formula I can have Structure P:

Structure P

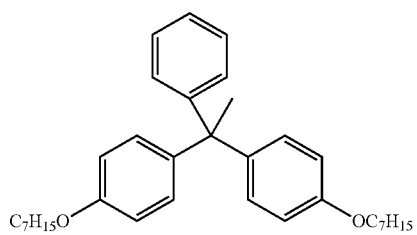

In an embodiment of the compound characterized by Formula I, X is C, and $R^1$ and $R^2$ can each independently be a methyl group or a phenyl group. In such an embodiment, the compound characterized by Formula I can have Structure P.

In an embodiment of the compound characterized by Formula I, X is C, and $R^1$ and $R^2$ can each independently be hydrogen, a $C_1$ to $C_{10}$ alkyl group, or a $C_6$ to $C_{10}$ aryl group.

In an embodiment of the compound characterized by Formula I, X is C, and $R^1$ and $R^2$ can each independently be a $C_1$ to $C_{10}$ alkyl group, or a $C_6$ to $C_{10}$ aryl group. In such an embodiment, the compound characterized by Formula I can have Structure P.

In an embodiment, $R^3$ and $R^{3'}$ can each independently be hydrogen or a $C_1$ to $C_4$ alkyl group, such as for example a methyl group, an ethyl group, a n-propyl group, an iso-propyl group, a n-butyl group, an iso-butyl group, a sec-butyl group, or a tert-butyl group.

In an embodiment, $R^3$ and $R^{3'}$ can each independently be hydrogen or a methyl group.

In an embodiment of the compound characterized by Formula I, X is O, and $R^3$ and $R^{3'}$ can each be hydrogen. In such an embodiment, the compound characterized by Formula I can have Structure A.

In another embodiment of the compound characterized by Formula I, X is S, and $R^3$ and $R^{3'}$ can each be hydrogen. In such an embodiment, the compound characterized by Formula I can have any of Structure B, Structure C, or Structure D.

In yet another embodiment of the compound characterized by Formula I, X is C, and $R^3$ and $R^{3'}$ can each be hydrogen. In such an embodiment, the compound characterized by Formula I can have any of Structure G, Structure H, Structure I, Structure J, Structure L, Structure M, Structure N, Structure O, or Structure P.

In still yet another embodiment of the compound characterized by Formula I, X is S, and $R^3$ and $R^{3'}$ can each be a methyl group. In such an embodiment, the compound characterized by Formula I can have Structure E.

In still yet another embodiment of the compound characterized by Formula I, X is S, and $R^3$ and $R^{3'}$ can each independently be hydrogen or a methyl group. In such an embodiment, the compound characterized by Formula I can have Structure F.

In still yet another embodiment of the compound characterized by Formula I, X is C, and $R^3$ and $R^{3'}$ can each be a methyl group. In such an embodiment, the compound characterized by Formula I can have Structure K.

In an embodiment, $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group. As used herein, the term "cycloalkyl group" is a general term that refers to any univalent group derived from a cycloalkane by removal of a hydrogen atom from any carbon atom of the cycloalkane ring. Cycloalkanes are saturated monocyclic hydrocarbons, and can be with or without side chains. Cycloalkanes and their corresponding cycloalkyl groups can also be substituted or unsubstituted. Whether the cycloalkyl is substituted or unsubstituted, the nomenclature of the cycloalkyl refers to the number of carbon atoms present in the cycloalkane ring. For example, a cyclobutyl group has 4 carbon atoms in the cycloalkyl ring; and a methylcyclopropyl group has 3 carbon atoms in the cycloalkyl ring, but a total of 4 carbon atoms.

In an embodiment of the compound characterized by Formula I, X is O, and $R^4$ and $R^{4'}$ can each be hydrogen. In such an embodiment, the compound characterized by Formula I can have Structure A.

In another embodiment of the compound characterized by Formula I, X is S, and $R^4$ and $R^{4'}$ can each be hydrogen. In such an embodiment, the compound characterized by Formula I can have any of Structure B, or Structure E.

In yet another embodiment of the compound characterized by Formula I, X is S, and $R^4$ and $R^{4'}$ can each independently be hydrogen or a tert-butyl group. In such an embodiment, the compound characterized by Formula I can have Structure F.

In still yet another embodiment of the compound characterized by Formula I, X is C, and $R^4$ and $R^{4'}$ can each be hydrogen. In such an embodiment, the compound characterized by Formula I can have any of Structure I, Structure J, Structure K, Structure M, Structure O, or Structure P.

In an embodiment, $R^4$ and $R^{4'}$ can each independently be a $C_1$ to $C_4$ alkyl group, such as for example a methyl group, an ethyl group, a n-propyl group, an iso-propyl group, a n-butyl group, an iso-butyl group, a sec-butyl group, or a tert-butyl group.

In an embodiment of the compound characterized by Formula I, X is S, and $R^4$ and $R^{4'}$ can each be a methyl group. In such an embodiment, the compound characterized by Formula I can have any of Structure C, or Structure D.

In another embodiment of the compound characterized by Formula I, X is C, and $R^4$ and $R^{4'}$ can each be a methyl group. In such an embodiment, the compound characterized by Formula I can have any of Structure H, or Structure N.

In an embodiment, $R^4$ and $R^{4'}$ can each independently be a $C_4$ to $C_{10}$ cycloalkyl group, such as for example a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In such an embodiment, the $C_4$ to $C_{10}$ cycloalkyl group can comprise a cyclohexyl group.

In an embodiment of the compound characterized by Formula I, X is C, and $R^4$ and $R^{4'}$ can each be a cyclohexyl group. In such an embodiment, the compound characterized by Formula I can have Structure L.

In an embodiment, $R^4$ and $R^{4'}$ can each independently be a $C_6$ to $C_{10}$ aryl group, such as for example a phenyl group, a substituted phenyl group, a tolyl group, a substituted tolyl group, a xylyl group, or a substituted xylyl group.

In an embodiment of the compound characterized by Formula I, X is C, and $R^4$ and $R^{4'}$ can each be a phenyl group. In such an embodiment, the compound characterized by Formula I can have Structure G.

In an embodiment, $R^5$ and $R^{5'}$ can each independently be a $C_4$ to $C_{10}$ alkyl group, such as for example a n-butyl group, an iso-butyl group, a sec-butyl group, a tert-butyl group, a pentyl group, a n-pentyl group, an iso-pentyl group, a sec-pentyl group, a hexyl group, a heptyl group, an octyl group, a nonyl group, or a decyl group.

In an embodiment, $R^5$ and $R^{5'}$ can both be a pentyl group or a heptyl group.

In an embodiment of the compound characterized by Formula I, X is S, and $R^5$ and $R^{5'}$ can each be a pentyl group. In such an embodiment, the compound characterized by Formula I can have any of Structure D, Structure E, or Structure F.

In another embodiment of the compound characterized by Formula I, X is C, and $R^5$ and $R^{5'}$ can each be a pentyl group. In such an embodiment, the compound characterized by Formula I can have any of Structure G, Structure K, or Structure L.

In yet another embodiment of the compound characterized by Formula I, X is O, and $R^5$ and $R^{5'}$ can each be a heptyl group. In such an embodiment, the compound characterized by Formula I can have Structure A.

In still yet another embodiment of the compound characterized by Formula I, X is S, and $R^5$ and $R^{5'}$ can each be a heptyl group. In such an embodiment, the compound characterized by Formula I can have any of Structure B, or Structure C.

In still yet another embodiment of the compound characterized by Formula I, X is C, and $R^5$ and $R^{5'}$ can each be a heptyl group. In such an embodiment, the compound characterized by Formula I can have any of Structure H, Structure I, Structure J, Structure M, Structure N, Structure O, or Structure P.

In an embodiment of the compound characterized by Formula I, X is C; $R^1$ and $R^2$ can each be hydrogen; and $R^5$ and $R^{5'}$ can both be a $C_4$ to $C_{10}$ alkyl group, such as for example a pentyl group or a heptyl group.

In an embodiment of the compound characterized by Formula I, X is C; $R^1$ and $R^2$ can each be hydrogen; and $R^5$ and $R^{5'}$ can each be a pentyl group. In another embodiment of the compound characterized by Formula I, X is C; $R^1$ and $R^2$ can each be hydrogen; and $R^5$ and $R^{5'}$ can each be a heptyl group.

In an embodiment of the compound characterized by Formula I, X is C; $R^1$ and $R^2$ can each be a methyl group; and $R^5$ and $R^{5'}$ can both be a $C_4$ to $C_{10}$ alkyl group, such as for example a pentyl group or a heptyl group.

In an embodiment of the compound characterized by Formula I, X is C; $R^1$ and $R^2$ can each be a methyl group; and $R^5$ and $R^{5'}$ can each be a pentyl group. In such an embodiment, the compound characterized by Formula I can have any of Structure G, or Structure L.

In another embodiment of the compound characterized by Formula I, X is C; $R^1$ and $R^2$ can each be a methyl group; and $R^5$ and $R^{5'}$ can each be a heptyl group. In such an embodiment, the compound characterized by Formula I can have any of Structure H, Structure J, or Structure N.

In an embodiment, $R^4$, $R^{4'}$, $R^5$, and $R^{5'}$ can each independently be a $C_1$ to $C_{10}$ alkyl group, a $C_4$ to $C_{10}$ cycloalkyl group, or a $C_6$ to $C_{10}$ aryl group, wherein the $C_4$ to $C_{10}$ cycloalkyl group can comprise a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In such an embodiment, the $C_4$ to $C_{10}$ cycloalkyl group can comprise a cyclohexyl group, such as for example in Structure L.

In an embodiment, $R^6$ and $R^{6'}$ can each independently be hydrogen or a $C_1$ to $C_6$ alkyl group, such as for example a methyl group, an ethyl group, a n-propyl group, an iso-propyl group, a n-butyl group, an iso-butyl group, a sec-butyl group, a tert-butyl group, a pentyl group, a n-pentyl group, an iso-pentyl group, a sec-pentyl group, or a hexyl group.

In an embodiment, $R^6$ and $R^{6'}$ can each independently be selected from the group consisting of a methyl group, an ethyl group, a n-propyl group, an iso-propyl group, a n-butyl group, an iso-butyl group, a sec-butyl group, a tert-butyl group, a pentyl group, a n-pentyl group, an iso-pentyl group, a sec-pentyl group and a hexyl group.

In an embodiment of the compound characterized by Formula I, X is O, and $R^6$ and $R^{6'}$ can each be hydrogen. In such an embodiment, the compound characterized by Formula I can have Structure A.

In another embodiment of the compound characterized by Formula I, X is S, and $R^6$ and $R^{6'}$ can each be hydrogen. In such an embodiment, the compound characterized by Formula I can have any of Structure B, or Structure C.

In yet another embodiment of the compound characterized by Formula I, X is S, and $R^6$ and $R^{6'}$ can each be a tert-butyl group. In such an embodiment, the compound characterized by Formula I can have any of Structure D, or Structure E.

In still yet another embodiment of the compound characterized by Formula I, X is S, and $R^6$ and $R^{6'}$ can each independently be hydrogen or a tert-butyl group. In such an embodiment, the compound characterized by Formula I can have Structure F.

In still yet another embodiment of the compound characterized by Formula I, X is C, and $R^6$ and $R^{6'}$ can each be hydrogen. In such an embodiment, the compound characterized by Formula I can have any of Structure G, Structure I, Structure L, Structure M, Structure N, Structure O, or Structure P.

In still yet another embodiment of the compound characterized by Formula I, X is C, and $R^6$ and $R^{6'}$ can each be methyl. In such an embodiment, the compound characterized by Formula I can have Structure H.

In still yet another embodiment of the compound characterized by Formula I, X is C, and $R^6$ and $R^{6'}$ can each be iso-propyl. In such an embodiment, the compound characterized by Formula I can have Structure J.

In still yet another embodiment of the compound characterized by Formula I, X is C, and $R^6$ and $R^{6'}$ can each be a tert-butyl group. In such an embodiment, the compound characterized by Formula I can have Structure K.

In an embodiment, $R^7$ and $R^{7'}$ can each independently be hydrogen or a $C_1$ to $C_4$ alkyl group, such as for example a methyl group, an ethyl group, a n-propyl group, an iso-propyl group, a n-butyl group, an iso-butyl group, a sec-butyl group, or a tert-butyl group.

In an embodiment, $R^7$ and $R^{7'}$ can each independently be hydrogen or a methyl group.

In an embodiment of the compound characterized by Formula I, X is O, and $R^7$ and $R^{7'}$ can each be hydrogen. In such an embodiment, the compound characterized by Formula I can have Structure A.

In another embodiment of the compound characterized by Formula I, X is S, and $R^7$ and $R^{7'}$ can each be hydrogen. In such an embodiment, the compound characterized by Formula I can have any of Structure B, Structure C, Structure D, or Structure E.

In yet another embodiment of the compound characterized by Formula I, X is S, and $R^7$ and $R^{7'}$ can each independently be hydrogen or a methyl group. In such an embodiment, the compound characterized by Formula I can have Structure F.

In still yet another embodiment of the compound characterized by Formula I, X is C, and $R^7$ and $R^{7'}$ can each be hydrogen. In such an embodiment, the compound characterized by Formula I can have any of Structure G, Structure H, Structure I, Structure J, Structure K, Structure L, Structure M, Structure N, Structure O, or Structure P.

In an embodiment, the compound characterized by Formula I can be produced by reaction of an intermediate phenol (AAA) with an alkylating agent $R^5X$ to yield Formula I according to the following reaction:

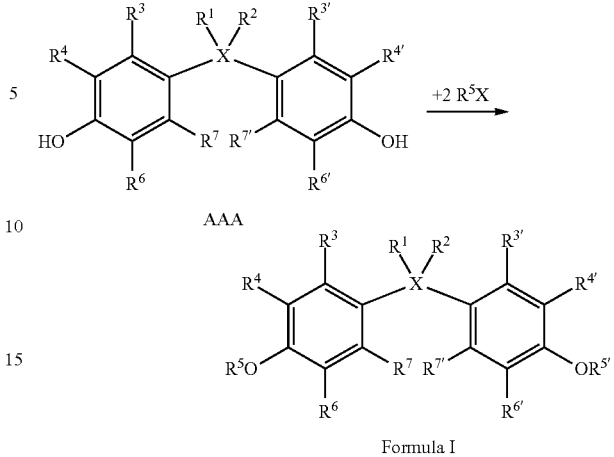

Other alkylating agents, such as alcohol derivatives (mesylates, tosylates, etc.) can be employed. Intermediate phenols AAA can be made by any suitable methodology. One example where X is C includes the reaction of a ketone with the appropriate phenol (BBB), according to the following reaction scheme:

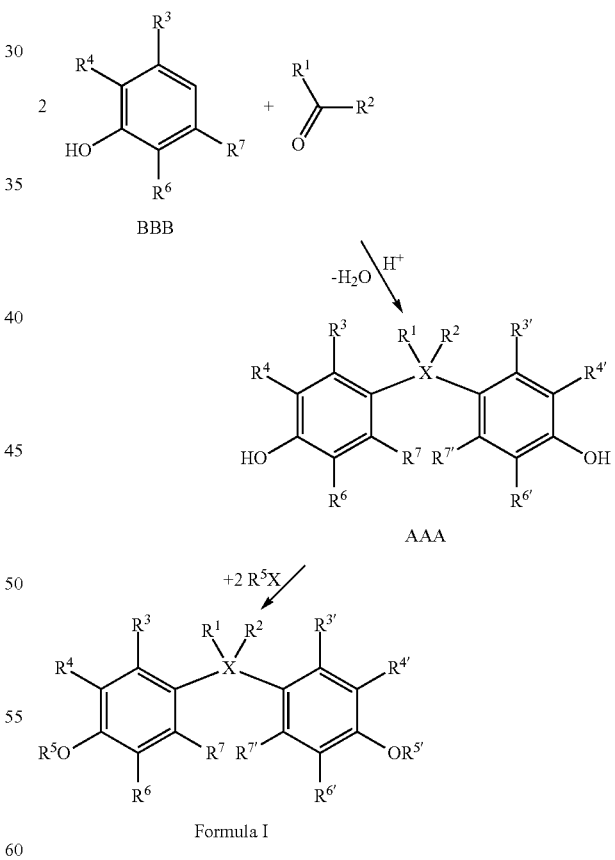

Subsequent alkylation as described leads to compounds of Formula I.

In an embodiment, a fuel marker comprising a compound characterized by Formula I as disclosed herein can be resistant to laundering. Generally, "laundering" of a fuel refers to processing or treating the fuel with laundering agents to partially or completely remove or mask the fuel marker such that the fuel cannot be properly authenticated. For purposes of the disclosure herein, the term "laundering agent" refers to any material or substance which is capable of partially or completely removing a fuel marker from a marked fuel composition.

Nonlimiting examples of laundering agents include strong acids, alkalis, absorbent materials, clay, carbon, active carbon, charcoal, active charcoal, paper filter, straw, microfilters, silica, silica gel, molecular sieves, adsorbent materials, and the like, or combinations thereof.

In an embodiment, the fuel marker can be present within the marked fuel composition in an amount of from about 1 ppb to about 50 ppm, alternatively from about 10 ppb to about 25 ppm, alternatively from about 100 ppb to about 10 ppm, alternatively from about 250 ppb to about 5 ppm, or alternatively from about 500 ppb to about 1 ppm, based on the total weight of the marked fuel composition.

In an embodiment, the marked fuel composition can be contacted with a heavy compound to yield a marked fuel mixture, wherein the heavy compound comprises a compound of Formula I having at least one atom replaced with an isotope tag (e.g., a heavy compound of Formula I). In such an embodiment, the heavy compound can be contacted in a known amount with the marked fuel composition, as will be disclosed in more detail later herein. Generally, an isotope tag refers to an atom that replaced in a molecule (e.g., a molecule of a compound of Formula I) another atom of the same element that has a different number of neutrons when compared to the atom that replaced it. For purposes of the disclosure herein, a fuel composition comprising a heavy compound will be referred to as a "marked fuel mixture," or simply "marked fuel composition."

Nonlimiting examples of isotope tags suitable for use in the present disclosure include deuterium ($^2$H), carbon-13 ($^{13}$C), oxygen-17 ($^{17}$O), sulfur-34 ($^{34}$S), and the like, or combinations thereof. For example, a commercially available phenol-$^2$H$_6$ (e.g., deuterated phenol d-BBB) can be reacted with ketones to create various deuterated bisphenol derivatives (e.g., d-AAA) according to the following reaction scheme:

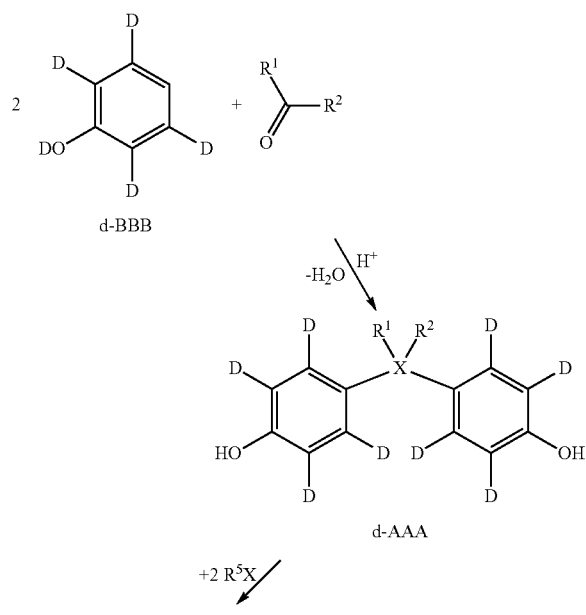

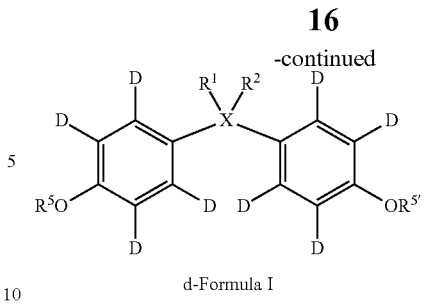

Subsequent alkylation yields the desired heavy compounds (e.g., deuterated compound of Formula I, d-Formula I). Performing the same synthesis with a commercially available $^{13}$C$_6$ labelled phenol would yield the $^{13}$C heavy compound. One skilled in the art would recognize that other isotopically labelled intermediates could be used to synthesize a variety of heavy compounds of various isotopic substitution.

In an embodiment, the marked fuel mixture comprises a heavy compound of Formula I, wherein the isotope tag comprises deuterium ($^2$H). In such an embodiment, the heavy compound of Formula I can further comprise other isotope tags, such as for example carbon-13 ($^{13}$C), oxygen-17 ($^{17}$O), sulfur-34 ($^{34}$S), and the like, or combinations thereof.

In an embodiment, the marked fuel mixture comprises a heavy compound of Formula I, wherein the isotope tag comprises carbon-13 ($^{13}$C). In such an embodiment, the heavy compound of Formula I can further comprise other isotope tags, such as for example deuterium ($^2$H), oxygen-17 ($^{17}$O), sulfur-34 ($^{34}$S), and the like, or combinations thereof.

In an embodiment, the marked fuel mixture comprises a heavy compound of Formula I, wherein the isotope tag comprises oxygen-17 ($^{17}$O). In such an embodiment, the heavy compound of Formula I can further comprise other isotope tags, such as for example deuterium ($^2$H), carbon-13 ($^{13}$C), sulfur-34 ($^{34}$S), and the like, or combinations thereof.

In an embodiment, the marked fuel mixture comprises a heavy compound of Formula I, wherein X can be O, wherein X comprises the isotope tag, and wherein the isotope tag comprises oxygen-17 ($^{17}$O). In such an embodiment, the heavy compound of Formula I can further comprise other isotope tags, such as for example deuterium ($^2$H), carbon-13 ($^{13}$C), sulfur-34 ($^{34}$S), and the like, or combinations thereof.

In an embodiment, the marked fuel mixture comprises a heavy compound of Formula I, wherein X can be S, and wherein the isotope tag comprises sulfur-34 ($^{34}$S). In such an embodiment, the heavy compound of Formula I can further comprise other isotope tags, such as for example deuterium ($^2$H), carbon-13 ($^{13}$C), oxygen-17 ($^{17}$O), and the like, or combinations thereof.

In an embodiment, the isotope tag can be introduced into the compound of Formula I to form a heavy compound by using any suitable methodology. In an embodiment, the isotope tag can be introduced into the compound of Formula I by chemical isotope exchange (i.e., exchange of isotopes between different types of molecules or ions in the course of a chemical reaction).

In some embodiments, the isotope tag can be introduced into the compound of Formula I by subjecting the compound of Formula I to a chemical isotope exchange with at least one isotope tag compound. Generally, an isotope tag compound refers to any compound containing an isotope tag (e.g., deuterium ($^2$H), carbon-13 ($^{13}$C), oxygen-17 ($^{17}$O), sulfur-34 ($^{34}$S), etc.), where such isotope tag compound can participate in a chemical isotope exchange reaction and/or a reaction for transferring the isotope tag to another compound.

In other embodiments, the isotope tag can be introduced into the compound of Formula I by subjecting a precursor of the compound of Formula I to a chemical isotope exchange with at least one isotope tag compound. For example, during the synthesis of the compound of Formula I, a precursor of the compound of Formula I can be subjected to a chemical isotope exchange with at least one isotope tag compound.

In yet other embodiments, the isotope tag can be introduced into the compound of Formula I by subjecting a first precursor of the compound of Formula I to a reaction with at least one isotope tag compound to yield a second precursor of the compound of Formula I, wherein the second precursor of the compound of Formula I comprises an isotope tag. In such embodiments, the second precursor of the compound of Formula I can be further converted to yield a heavy compound of Formula I, wherein the heavy compound of Formula I comprises an isotope tag.

In still yet other embodiments, the isotope tag can be introduced into the compound of Formula I by subjecting a precursor of the compound of Formula I to a reaction with at least one isotope tag compound to yield a heavy compound of Formula I, wherein the heavy compound of Formula I comprises an isotope tag. In an embodiment, the isotope tag can be located at any position in the structure, alternatively the structure comprises isotope tags at multiple positions. In an embodiment, the position for isotopic substitution can be chosen to lead to a significant shift in the mass-to-charge ratio (m/z) of the heavy compound. For example, the position for isotopic substitution can be chosen to provide a m/z shift of from about 4 atomic mass units (AMU) to about 12 AMU, alternatively greater than about 4 AMU, alternatively greater than about 8 AMU, or alternatively greater than about 12 AMU.

In some embodiments, a precursor of the compound of Formula I (e.g., a first precursor of the compound of Formula I, a second precursor of the compound of Formula I, etc.) can comprise an isotope tag compound, such as for example deuterated 1-bromopentane (1-bromopentane-$d_{11}$, $CsD_{11}Br$), deuterated 1-bromoheptane (1-bromoheptane-$d_{15}$, $C_7D_{15}Br$), deuterated phenol ($C_6D_5OD$), and the like, or combinations thereof.

Nonlimiting examples of isotope tag compounds suitable for use in the present disclosure include deuterated 1-bromopentane (1-bromopentane-$d_{11}$, $CsD_{11}Br$), deuterated 1-bromoheptane (1-bromoheptane-$d_{15}$, $C_7D_5Br$), deuterated phenol ($C_6D_5OD$), deuterated water (deuterium oxide, $D_2O$), deuterated hydrochloric acid (DCl), deuterated acetic acid ($CD_3COOD$), deuterated acetone ($CD_3COCD_3$), deuterated methanol ($CD_3OD$), deuterated acetonitrile ($CD_3CN$), deuterated benzene ($C_6D_6$), deuterated chloroform ($CDCl_3$), deuterated cyclohexane ($C_6D_{12}$), deuterated N,N-dimethylformamide ($DCON(CD_3)_2$), deuterated dimethyl sulphoxide ($CD_3SOCD_3$), deuterated ethanol ($C_2D_5OD$), deuterated methylene chloride ($CD_2Cl_2$), deuterated nitromethane ($CD_3NO_2$), deuterated pyridine ($C_5D_5N$), deuterated tetrahydrofuran ($C_4D_8O$), deuterated toluene ($C_6D_5CD_3$), deuterated trifluoroacetic acid ($CF_3COOD$); acetaldehyde-1-$^{13}C$, acetaldehyde-1,2-$^{13}C_2$, acetic acid-1-$^{13}C$, acetic acid-2-$^{13}C$, acetic acid-1,2-$^{13}C$, acetic anhydride-1,1-$^{13}C_2$, acetic anhydride-2,2-$^{13}C_2$, acetic anhydride-1,1,2,2-$^{13}C_4$, acetone-2-$^{13}C$, acetone-1,3-$^{13}C_2$, acetone-1,2,3-$^{13}C_3$, acetonitrile-1-$^{13}C$, acetonitrile-2-$^{13}C$, acetonitrile-1,2-$^{13}C_2$, acetophenone-1-$^{13}C$, acetophenone-2-$^{13}C$, acetyl chloride-1-$^{13}C$, acetyl chloride-2-$^{13}C$, acetyl chloride-1,2-$^{13}C_2$, aniline-$^{13}C_6$, aniline chloride-$^{13}C_6$, aniline sulfate-$^{13}C_6$, benzaldehyde-carbonyl-$^{13}C$, benzene-$^{13}C_6$, benzenesulfonyl chloride-$^{13}C_6$, benzoic acid-carbonyl-$^{13}C$, benzophenone-$^{13}C$ (carbonyl labeled), benzophenone-$^{13}C_{12}$ (ring labeled), benzoyl chloride-$^{13}C$ (ring labeled), benzoyl chloride-carbonyl-$^{13}C$, benzyl alcohol-$^{13}C_6$ (ring labeled), tert-butyl chloride-$^{13}C$, carbon dioxide-$^{13}C$, carbon disulfide-$^{13}C$, carbon monoxide-$^{13}C$, carbon tetrachloride-$^{13}C$, chloroacetic acid-1-$^{13}C$, chloroacetic acid-2-$^{13}C$, chloroacetic acid-1,2-$^{13}C_2$, chlorobenzene-$^{13}C_6$, chloroethane-1,2-$^{13}C_2$, chloroform-$^{13}C$, chloromethane-$^{13}C$, cyanoacetic acid-1-$^{13}C$, cyanoacetic acid-2-$^{13}C$, cyanoacetic acid-$^{13}C$ (cyanide labeled), dichloromethane-$^{13}C$, dimethyl formamide-carbonyl-$^{13}C$, dimethyl-$^{13}C_2$ sulfoxide, ethyl acetate-1-$^{13}C$, ethyl acetate-2-$^{13}C$, ethyl alcohol-1-$^{13}C$, ethyl alcohol-2-$^{13}C$, ethyl alcohol-1,2-$^{13}C_2$, ethylamine-1-$^{13}C$, ethyl chloride-1,2-$^{13}C_2$, ethylene oxide-1,2-$^{13}C_2$, formaldehyde-$^{13}C$, formamide-$^{13}C$, hexane-1-$^{13}C$, 1,6-hexanediamine-1,6-$^{13}C_2$, isobutane-2-$^{13}C$, isopropanol-2-$^{13}C$, methane-$^{13}C$, methyl alcohol-$^{13}C$, methylamine-$^{13}C$, methyl bromide-$^{13}C$, methyl chloride-$^{13}C$, methylene chloride-$^{13}C$, methyl formate-$^{13}C$, nitrobenzene-$^{13}C_6$, nitromethane-$^{13}C$, phosgene-$^{13}C$, propane-2-$^{13}C$, 1,3-propanediol-2-$^{13}C$, propene-1-$^{13}C$, propene-2-$^{13}C$, propene-3-$^{13}C$, sodium acetate-1-$^{13}C$, sodium acetate-2-$^{13}C$, sodium acetate-1,2-$^{13}C_2$, sodium bicarbonate-$^{13}C$, sodium carbonate-$^{13}C$, sodium cyanide-$^{13}C$, sodium formate-$^{13}C$, sodium thiocyanate-$^{13}C$, thiourea-$^{13}C$, toluene-7-$^{13}C$, trichloroacetic acid-1,2-$^{13}C_{20}$, urea-$^{13}C$; water-$^{17}O$, acetaldehyde-$^{17}O$, adipic acid-$^{17}O_4$, ammonium nitrate-$^{17}O_3$, benzophenone-$^{17}O$, carbon dioxide-$^{17}O_2$, carbon monoxide-$^{17}O$, carbonyl sulfide-$^{17}O$, cyclopentanone-$^{17}O$, deuterium oxide-$^{17}O$, dimethyl formamide-$^{17}O$, ethanol-$^{17}O$, formic acid-$^{17}O$, nitrous oxide-$^{17}O$, oxygen-$^{17}O_2$, phosgene-$^{17}O$, urea-$^{17}O$; carbon disulfide-$^{34}S$, carbonyl sulfide-$^{34}S$, magnesium sulfate-$^{34}S$, potassium thiocyanate-$^{34}S$, sulfur-$^{34}S$, sodium sulfate-$^{34}S$, sulfur dioxide-$^{34}S$, sulfuric acid-$^{34}S$, thioacetamide-$^{34}S$, thioacetic acid-$^{34}S$, thiourea-$^{34}S$; deuterated acetic acid-1-$^{13}C$ ($CD_3CO_2D$), deuterated acetic acid-2-$^{13}C$ ($CD_3CO_2D$), deuterated acetone-1,3-$^{13}C_2$ ($CD_3COCD_3$), deuterated acetone-1,2,3-$^{12}C_3$($CD_3COCD_3$), deuterated acetonitrile-1,2-$^{12}C$ ($CD_3CN$), deuterated acetonitrile-$^{15}N$ ($CD_3CN$), deuterated acetonitrile-1-$^{13}C$ ($CD_3CN$), deuterated ammonia-$^{15}N$ ($ND_3$), deuterated ammonium chloride-$^{15}N$ ($ND_4Cl$), deuterated ammonium sulfate-$^{15}N_2$ (($ND_4)_2SO_4$), deuterated methane-$^{13}C$ ($CH_3D$), deuterated methane-$^{13}C$ ($CD_4$), deuterated methyl alcohol-$^{13}C$ ($CD_3OD$), deuterated sodium acetate-1-$^{13}C$ ($CD_3CO_2Na$), deuterated sodium acetate-2-$^{13}C$ ($CD_3CO_2Na$), deuterated urea-$^{13}C$ ($ND_2COND_2$), deuterated urea-$^{13}C,^{15}N_2$ ($ND_2COND_2$); carbon dioxide-$^{13}C,^{17}O$; cyanamide-$^{13}C,^{15}N_2$; formamide-$^{13}C,^{15}N$; thiourea-$^{13}C,^{15}N_2$; urea-$^{13}C,^{15}N_2$; and the like, or combinations thereof.

In some embodiments, the isotope tag compounds can comprise deuterated 1-bromopentane (1-bromopentane-$d_{11}$, $CsD_{11}Br$). In other embodiments, the isotope tag compounds can comprise deuterated 1-bromoheptane (1-bromoheptane-$d_{15}$, $C_7D_{15}Br$). In yet other embodiments, the isotope tag compounds can comprise deuterated phenol ($C_6D_5OD$).

As will be appreciated by one of skill in the art, and with the help of this disclosure, more than one isotope tag can be introduced into a chemical compound, such as for example 2, 3, 4, 5, 6, 7, 8, 9, 10, or more isotope tags. In some embodiments, at least two of the isotope tags of the compound of Formula I are the same. In other embodiments, at least two of the isotope tags of the compound of Formula I are different. In yet other embodiments, at least two of the isotope tags of the compound of Formula I can be the same, and/or at least two of the isotope tags of the compound of Formula I can be different.

In an embodiment of a heavy compound of Formula I (e.g., deuterated compound of Formula I, d-Formula I), X is S. In such an embodiment, the heavy compound of Formula I can have any of deuterated Structure B (d-Structure B), or deuterated Structure F (d-Structure F):

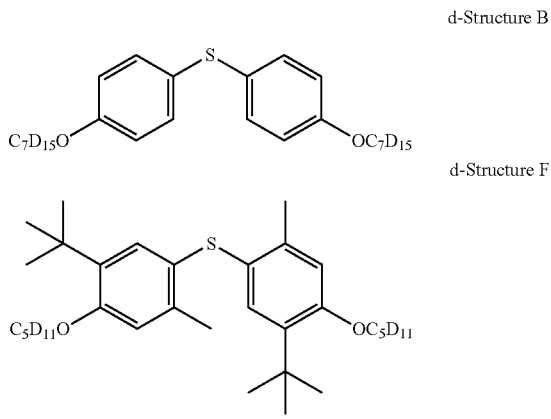

d-Structure B d-Structure F

In an embodiment, the heavy compound can be present within the marked fuel mixture in an amount (e.g., can be added to a fuel composition in a known amount) of from about 1 ppb to about 50 ppm, alternatively from about 10 ppb to about 25 ppm, alternatively from about 100 ppb to about 10 ppm, alternatively from about 250 ppb to about 5 ppm, or alternatively from about 500 ppb to about 1 ppm, based on the total weight of the marked fuel mixture.

In an embodiment, the marked fuel composition can be prepared by using any suitable methodology. In an embodiment, a method of forming a marked fuel composition can comprise contacting (a) a fuel, and (b) a fuel marker comprising at least one compound characterized by Formula I.

In some embodiments, the fuel marker comprising at least one compound characterized by Formula I can be added to the fuel to form the marked fuel composition. In other embodiments, the fuel can be added to the fuel marker comprising at least one compound characterized by Formula I to form the marked fuel composition.

In some embodiments, the fuel marker can be contacted with the fuel in powder form. In other embodiments, the fuel marker can be contacted with the fuel as a fuel marker solution, wherein the fuel marker can be solubilized in one or more solvents to form a fuel marker solution. In an embodiment, a solvent suitable for use in the present disclosure is characterized by a flash point greater than about 60° C. and miscibility with the fuels disclosed herein. Nonlimiting examples of solvents suitable for use in the present disclosure for making a fuel marker solution include hydrocarbons, aromatic hydrocarbons, halogenated hydrocarbons, ethers, carbonates, esters, ketones, aldehydes, alcohols, nitriles, and combinations thereof. Polar solvents which can be utilized include without limitation water, ethers, carbonates, esters, ketones, aldehydes, alcohols, nitriles, and mixtures thereof; alternatively, ethers, carbonates, esters, ketones, aldehydes, alcohols, nitriles, and mixtures thereof. Aprotic polar solvents which can be utilized include without limitation ethers, esters, ketones, aldehydes, nitriles, and mixtures thereof; alternatively, ethers, nitriles, and mixtures thereof. Non-polar solvents include without limitation hydrocarbons, aromatic hydrocarbons, halogenated hydrocarbons, or mixtures thereof; alternatively, a hydrocarbon; alternatively, an aromatic hydrocarbon; or alternatively, a halogenated hydrocarbon. In another embodiment, the solvent comprises aromatic solvent 150 and 200, N-methylpyrollidone, 2-ethylhexanol, hydrocarbon solvents such as mineral spirits, and the like, or combinations thereof.

In an embodiment, an additive pack can comprise the fuel marker. In such an embodiment, the additive pack comprises a fuel marker solution. In an embodiment, the additive pack can further comprise a detergent, a surfactant, a lubricant, an octane enhancer, a crystallization inhibitor, a freeze point depressant, and the like, or combinations thereof. In an embodiment, the additive pack comprising the fuel marker can be contacted with the fuel to form a marked fuel composition.

In embodiments where an additive pack is used, the fuel marker comprising a compound characterized by Formula I can be mixed with the additive pack prior to adding the additive pack to the fuel. In an alternative embodiment, where the additive pack is used, the fuel marker comprising the compound characterized by Formula I and the additive pack can be added to the fuel at the same time, without prior mixing of the fuel marker with the additive pack. In other embodiments, where the additive pack is used, the additive pack and the fuel marker comprising the compound characterized by Formula I can be added to the fuel at different times. For example, the additive pack can be added to the fuel first, and the fuel marker comprising the compound characterized by Formula I can be added to the fuel second. Further, for example, the fuel marker comprising the compound characterized by Formula I can be added to the fuel first, and the additive pack can be added to the fuel second.

As will be appreciated by one of skill in the art, and with the help of this disclosure, whether the fuel marker is contacted with the fuel in powder form, as a fuel marker solution, or as part of an additive pack, the concentration of the fuel marker in the marked fuel composition can be known (e.g., calculated) based on the amount of powder used, the concentration of the fuel marker in the fuel marker solution or the additive pack, the amount of fuel marker solution or additive pack used, etc.

In an embodiment, the fuel can be contained in a container, a storage container, transport container, a tanker truck, tanker ship, pipeline, or any other suitable means for transporting fuel from one place to another.

In an embodiment, the fuel can be in a pipeline. For example, the fuel could be transported through the pipeline from a processing plant to a storage container. In such an embodiment, the fuel marker can be injected through an injection valve into a fuel stream travelling through the pipeline.

In an embodiment, the fuel can be in a transport container (e.g., tanker truck, a tanker ship, etc.). In such an embodiment, the fuel marker can be added to the transport container through a port located on the transport container above the level of the fuel in the container. Further, the fuel marker can be injected through an injection valve into the transport container, wherein the injection valve can be located below the level of the fuel in the container.

In an embodiment, the storage container comprising the fuel can be a static storage container (e.g., the storage container is immobile, does not move or travel), wherein the static storage container could be located above ground, below ground, or partially below ground and partially above ground. In such an embodiment, the fuel marker can be added to the static storage container through a port located on the static storage container above the level of the fuel in the container. Further, the fuel marker can be injected through an injection valve into the static storage container, wherein the injection valve can be located below the level of the fuel in the container.

In an embodiment, the storage container comprising the fuel can be a mobile storage container (e.g., the storage container is mobile, it can move or travel). In such an embodiment, the fuel marker can be added to the mobile storage container through a port located on the mobile storage container above the level of the fuel in the container. Further, the fuel marker can be injected through an injection valve into the mobile storage container, wherein the injection valve can be located below the level of the fuel in the container.

In some embodiments, the fuel marker can be added to a dry container (e.g., a container comprising no fuel). In such embodiments, the fuel can be added to the container subsequent to the addition of the fuel marker to the container.

In an embodiment, a method of determining (e.g., evaluating, assessing, estimating, etc.) adulteration of a fuel can comprise subjecting to an analytical technique a marked fuel composition comprising a fuel and a fuel marker, wherein the fuel marker comprises a compound characterized by Formula I.

In an embodiment, the analytical technique can comprise GC-MS, nuclear magnetic resonance (NMR) spectroscopy, $^{13}C$ NMR spectroscopy, surface enhanced Raman scattering spectroscopy, and the like, or combinations thereof.

In an embodiment, a method of determining adulteration of a fuel can comprise (i) acquiring a fuel sample; (ii) subjecting the fuel sample to the analytical technique to determine fuel sample data (e.g., marker concentration); and (iii) comparing the fuel sample data to a target marking level (e.g., target marker concentration; control data) used to mark the fuel. As will be appreciated by one of skill in the art, and with the help of this disclosure, the target marker concentration of the marked fuel composition is generally acquired for marked fuel compositions at a point where the fuel sample data is known, e.g., prior to any possibility of adulteration. For example, acquisition of the target marker concentration at the place of marking as quality standard can provide for dosing of the marked fuels at the target marking level.

In some embodiments, a method of determining adulteration of a fuel can be performed without addition of standards to the fuel sample. In an embodiment, a method of determining adulteration of a fuel excludes the addition of standards to the fuel sample.

In other embodiments, a method of determining adulteration of a fuel can require addition of a standard (e.g., internal standard) to the fuel sample, such as for example a heavy compound, as will be described in more detail later herein.

In an embodiment, if the fuel sample data (e.g., marker concentration) matches the control data of the marked fuel composition (e.g., target marker concentration), the fuel can be deemed to be unadulterated fuel. As will be appreciated by one of skill in the art, and with the help of this disclosure, the "matching" of the fuel sample data (e.g., marker concentration) with the control data of the marked fuel composition (e.g., target marker concentration) has to be within experimental error limits for the fuel sample to be deemed unadulterated, and such experimental error limits are dependent on the particular analytical technique used, the analytical instrumentation used for the detection and analysis of the fuel marker, etc. The matching of data could include measuring a marker concentration to determine if the fuel has been diluted, by comparing the marker concentration with the target marker concentration. The matching of data could also include the detection of a marker that has been added to a potential adulterant and should not be present in the fuel. Quantification of the amount of such a marker would indicate the extent of dilution by the potential adulterant.

In an embodiment, if the fuel sample data does not match the control data of the marked fuel composition, the fuel can be deemed to be adulterated fuel. As will be appreciated by one of skill in the art, and with the help of this disclosure, the difference between the fuel sample data and the control data of the marked fuel composition has to fall outside of experimental error limits (e.g., the fuel sample data and the control data of the marked fuel composition do not match) for the sample to be deemed adulterated, and such experimental error limits are dependent on the particular analytical technique used, the analytical instrumentation used for the detection and analysis of the fuel marker, etc. Methods for matching and determination of the extent of adulteration of a marked fuel, as well as methods for fuel authentication by using more than one marker, are disclosed in greater detail in U.S. Pat. No. 8,592,213, which is incorporated by reference herein in its entirety.

In an embodiment, a method of determining adulteration of a fuel can be performed in the field (e.g., on location, direct detection, etc.). Determining adulteration of a fuel in the field can include testing at any location where a fuel can be found. Determining adulteration in the field can allow for rapid qualitative and/or quantitative assessment of the presence and/or amount of fuel marker in a fuel sample.

In another embodiment, a fuel sample can be collected from a first location (e.g., a gas station), and then transported to a second location (e.g., a laboratory) for further testing, e.g., determining adulteration.

In an embodiment, a method of determining adulteration of a fuel can comprise contacting a marked fuel composition with a heavy compound to yield a marked fuel mixture, wherein the heavy compound comprises a compound of Formula I having at least one atom replaced with an isotope tag. In such an embodiment, a known amount of the heavy compound can be contacted with (e.g., added to) the marked fuel composition to yield the marked fuel mixture (e.g., wherein the heavy compound can be present in the marked fuel mixture in a known amount). The heavy compound can be used as an internal standard.

In an embodiment, the method of determining adulteration of a fuel can further comprise subjecting the marked fuel mixture to an analytical technique.

In an embodiment, the analytical technique can evaluate fuel adulteration by (i) determining the presence of the heavy compound in the marked fuel mixture; and (ii) determining a ratio of an amount of the compound characterized by Formula I to the known amount of the heavy compound in the marked fuel mixture.

In an embodiment, (i) determining the presence of the heavy compound in the marked fuel mixture can further comprise determining the presence of the compound characterized by Formula I in the marked fuel mixture.

In an embodiment, (ii) determining a ratio of an amount of the compound characterized by Formula I to a known amount of the heavy compound in the marked fuel mixture further comprises calculating the amount of the compound characterized by Formula I in the marked fuel mixture.

As will be appreciated by one of skill in the art, and with the help of this disclosure, the compound characterized by Formula I and the heavy compound comprising a compound of Formula I having at least one atom replaced with an isotope tag can have the same chemical and physical properties, such as for example, melting temperature, solubility, density, absorption, reactivity, chemical stability, elution time, etc. Further, as will be appreciated by one of skill in the art, and with the help of this disclosure, when present in the same composition (e.g., marked fuel mixture), the compound characterized by Formula I and the heavy compound comprising a compound of Formula I having at least one atom replaced with an isotope tag are challenging to separate from each other by conventional analytical methods, such as chromatography, and will be analyzed simultaneously, or nearly simultaneously by the analytical technique.

In an embodiment, the compound characterized by Formula I and the heavy compound comprising a compound of Formula I having at least one atom replaced with an isotope tag can each display analytical signals that are different (e.g., distinct, dissimilar, etc.) from each other, thereby enabling simultaneous detection of both the compound characterized by Formula I and the heavy compound. As will be appreciated by one of skill in the art, and with the help of this disclosure, isotope tags have unique analytical signals and can be detected by a variety of analytical techniques, and such unique analytical signals do not appear in the absence of the isotope tag.

In an embodiment, the marked fuel mixture can be subjected to the analytical technique to record an analytical signal for the compound characterized by Formula I and an analytical signal for the heavy compound in the marked fuel mixture. In such an embodiment, the analytical signal for the compound characterized by Formula I and the analytical signal for the heavy compound in the marked fuel mixture can be different.

In some embodiments, the analytical signal for the compound characterized by Formula I and the analytical signal for the heavy compound in the marked fuel mixture can correlate (e.g., be proportional, be directly proportional, etc.) with the amount of the compound characterized by Formula I and the amount (e.g., known amount) of the heavy compound in the marked fuel mixture, respectively. In such embodiments, a ratio of the analytical signal for the compound characterized by Formula I to the analytical signal for the heavy compound in the marked fuel mixture can be the same as (e.g., equal to) the ratio of the amount of the compound characterized by Formula I to the known amount of the heavy compound in the marked fuel mixture. The ratio of the amount of the compound characterized by Formula I to the known amount of the heavy compound in the marked fuel mixture can be used for calculating the amount of the compound characterized by Formula I in the marked fuel mixture based on the known amount of the heavy compound in the marked fuel mixture. As will be appreciated by one of skill in the art, and with the help of this disclosure, the heavy compound is used as an internal standard for determining the amount of the compound characterized by Formula I in the marked fuel mixture. The internal standard is held fixed at a predetermined concentration that will be used in the analysis and the analyte (e.g., compound characterized by Formula I) concentration is varied. The resulting data is used then to generate a calibration curve that can be utilized in quantitating the fuel sample data (e.g., fuel marker concentration).

The selection of an appropriate internal standard can be very important in generating the most accurate results in this particular type of analysis (e.g., fuel authentication using a heavy compound as internal standard). For GC-MS analysis, deuterated isotopologues can often be the best choice if available, as they can very closely match a retention time of the fuel marker, and can produce a signal on a different mass channel of a MS detector, which would not interfere with integration of the fuel marker signal. Alternatively, a structural isomer of a fuel marker structure can be used to produce similar results, or a closely related structure in the same or very similar chemical class can be utilized. Without wishing to be limited by theory, the more structurally similar the internal standard is to the fuel marker structure, the more accurate the results will be.

In some embodiments, an internal standard can be co-submitted or co-injected (e.g., via an automated liquid injector) along with an unknown sample (e.g., fuel sample) for analysis (e.g., GC-MS analysis). In other embodiments, an internal standard solution can be mixed with an unknown solution (e.g., fuel sample to be authenticated) to form a combined solution, and the combined solution can be submitted or injected for analysis (e.g., GC-MS analysis). As will be appreciated by one of skill in the art, and with the help of this disclosure, whether the internal standard and the fuel sample are pre-mixed or co-injected, similar results will be obtained from the GC-MS analysis.

In an embodiment, the method of determining adulteration of a fuel can comprise determining an amount (e.g., concentration) of a fuel marker (e.g., a compound characterized by Formula I) in the fuel sample, based on the fuel sample data (e.g., analytical signal).

In an embodiment, a method of determining adulteration of a fuel can comprise (i) acquiring a fuel sample; (ii) adding a known amount of the heavy compound to the fuel sample to yield a marked fuel mixture; (iii) subjecting the marked fuel mixture to the analytical technique to record an analytical signal for the compound characterized by Formula I and an analytical signal for the heavy compound; (iv) comparing the analytical signal for the known amount of heavy compound to the analytical signal for the compound characterized by Formula I; (v) determining a ratio of an amount of the compound characterized by Formula I to the known amount of the heavy compound in the marked fuel mixture; and (vi) calculating the amount of the compound characterized by Formula I in the marked fuel mixture. In such an embodiment, (i) acquiring a fuel sample can further comprise determining the presence of the compound characterized by Formula I in the fuel sample.

In an embodiment, the analytical technique can evaluate fuel adulteration by determining the amount of the compound characterized by Formula I in the marked fuel mixture, e.g., the amount of the compound characterized by Formula I in the marked fuel composition, the amount of the compound characterized by Formula I in the fuel sample, etc.

In an embodiment, if the amount of the compound characterized by Formula I in the fuel sample matches the control data (e.g., target marker concentration) of the marked fuel composition, the fuel can be deemed to be unadulterated fuel.

In an embodiment, if the amount of the compound characterized by Formula I in the fuel sample does not match the control data (e.g., target marker concentration) of the marked fuel composition, the fuel can be deemed to be adulterated fuel.

In an embodiment, if a compound characterized by Formula I is detected in an unmarked fuel, the fuel can be deemed to be adulterated fuel.

In an embodiment, if a compound characterized by Formula I is detected in a fuel marked with a marker other than the compound characterized by Formula I, the resulting fuel can be deemed to be adulterated fuel.

In an embodiment, a method of determining adulteration of a fuel can comprise (i) acquiring a fuel sample; (ii) subjecting the fuel sample to GC-MS to yield GC-MS data; and (iii) comparing the GC-MS data of the fuel sample with the GC-MS data of the marked fuel composition (e.g., control data of the marked fuel composition). In such an embodiment, the method can further comprise determining an amount of the compound characterized by Formula I present in the marked fuel composition and/or the fuel sample based on the GC-MS data.

GC-MS enables both qualitative and quantitative analysis of mixtures of compounds. Generally, GC-MS is a combination of two techniques into a single method of analysis for mixtures of compounds (e.g., marked fuel composition, marked fuel mixture, fuel sample, etc.). Gas chromatography (GC) is a very prevalent technique for the separation of complex mixtures such as petroleum products because of its high separation power and low limits of detection when paired with a suitable detector like a mass spectrometer. GC separates components of a mixture based on differences in the chemical properties between different mixture components and based on their relative affinities for a stationary phase of a GC column. As a sample (e.g., fuel sample) travels along the GC column, the mixture components separate (e.g., some components will travel faster than others). The mixture components will ideally exit the GC individually, and would enter the mass spectrometer (MS) for further characterization. As will be appreciated by one of skill in the art, and with the help of this disclosure, sometimes certain mixture components will travel together along the GC column, and will enter the MS together; however, MS has the ability to discriminate between certain mixture components that elute (come off) together from the GC column. The different compounds can be retained by the GC column and then elute from the GC column at different times (e.g., retention times), and this can allow the MS downstream to analyze (e.g., capture, ionize, accelerate, deflect, detect, etc.) individually the eluted components. MS characterizes each component entering from the GC individually by ionizing molecules (e.g., breaking each molecule into ionized fragments) and detecting these fragments using their mass-to-charge ratio. Nonlimiting examples of ionization methods suitable for use in MS include electron ionization (also known as electron impact), chemical ionization, electrospray ionization, matrix-assisted laser desorption/ionization, inductively coupled plasma, photoionization, glow discharge, field desorption, fast atom bombardment, thermospray, spark ionization, thermal ionization, and the like, or combinations thereof.

In an embodiment, the fuel sample and/or the marked fuel mixture can be subjected to GC-MS, wherein the ionization method of the MS comprises electron ionization.

Generally, MS allows identification of amount and type of compounds (e.g., molecules) present in a sample by measuring the mass-to-charge ratio and abundance of gas-phase ions. MS ionizes chemical compounds to generate charged molecules or molecule fragments and measures their mass-to-charge ratios. The molecule fragments are actually charged ions with a certain mass. The mass of the fragment divided by the charge is called the "mass-to-charge ratio" (m/z). Since most fragments have a charge of +1, the mass-to-charge ratio usually represents the molecular weight of the fragment. MS produces a mass spectrum for each analyzed compound, wherein the x-axis represents the mass-to-charge ratio and wherein the y-axis represents the signal intensity (abundance) for each of the fragments detected. As will be appreciated by one of skill in the art, and with the help of this disclosure, the mass spectrum produced by a given compound is essentially the same every time, and can be regarded as a "fingerprint" for the compound. This fingerprint can be used to identify the compound.

The y-axis in the mass spectrum can be a relative abundance axis. The peak with the greatest abundance is usually referred to as a "base peak," and for the purpose of making a relative abundance axis the base peak intensity is set to 100%, such that the entire mass spectrum is normalized to the base peak. In some embodiments, the molecular ion peak can be the base peak. In such embodiments, the entire mass spectrum can be normalized to the molecular ion peak, wherein the molecular ion peak has 100% relative abundance.

In other embodiments, a peak other than the molecular ion peak can be the base peak. In such embodiments, all other fragment peaks and/or molecular ion peak can be normalized with respect to the base peak, wherein the base peak has 100% relative abundance, to produce normalized fragment peaks and/or a normalized molecular ion peak.

If a sample forms a molecular ion, it is likely to be the heaviest ion (e.g., ion with the greatest mass-to-charge ratio value) in the mass spectrum, and as such allows the identification of the compound by its molecular weight. The molecular ion is generally an ion formed by the removal from (positive ions) or addition to (negative ions) a molecule of one electron without fragmentation of the molecular structure. The mass of the molecular ion corresponds to the sum of the masses of the most abundant naturally occurring isotopes of the various atoms that make up the molecule (with a correction for the masses of the electron(s) lost or gained). As will be appreciated by one of skill in the art, and with the help of this disclosure, some compounds do not have a molecular ion present on the mass spectrum, because all of the molecular ions break into fragments.

As will be appreciated by one of skill in the art, and with the help of this disclosure, the way a compound (e.g., a molecule) fragments depends upon the type of ionization used to ionize the compound. Further, as will be appreciated by one of skill in the art, and with the help of this disclosure, the fragmentation pattern formed by an analyte will depend on the ionization conditions and therefore is a controllable parameter within the analysis.

In an embodiment, a fuel sample and/or a marked fuel mixture can be subjected to GC-MS, wherein the MS ionization method comprises electron ionization (EI), and wherein the ionization energy of the MS can be equal to or greater than about 70 eV, which effectively ionizes most organic compounds. In an embodiment, the extent of ionization is controlled to preferentially afford ionization of the analyte and heavy marker. This can be achieved by a variety of methods, including varying the EI voltage, use of chemical ionization with different chemical potentials, and photoionization with different strengths and wavelengths of light as non-limiting examples.

In an embodiment, the compound characterized by Formula I when subjected to GC-MS using electron ionization can produce at least one ion having a mass-to-charge ratio of equal to or greater than about 300, alternatively from about 300 to about 600, alternatively from about 400 to about 600, or alternatively from about 500 to about 600, at an ionization energy of equal to or greater than about 70 eV.

In an embodiment, the compound characterized by Formula I when subjected to GC-MS using electron ionization can produce at least one molecular ion having a mass-to-charge ratio of equal to or greater than about 300, alternatively from about 300 to about 600, alternatively from about 400 to about 600, or alternatively from about 500 to about 600, at an ionization energy of equal to or greater than about 70 eV.

In an embodiment, the marked fuel composition can comprise at least two compounds characterized by Formula I, wherein the marked fuel composition can be subjected to GC-MS. Each of the fuel markers of the marked fuel composition can display a unique mass spectrum profile, and can provide for authenticating a fuel sample. GC-MS can yield a mass spectrum displaying simultaneously information about more than one fuel marker, provided that the fuel markers have a different molecular weight, e.g., their molecular ions have different mass-to-charge ratios.

In an embodiment, a method of determining adulteration of a fuel can comprise subjecting to GC-MS a marked fuel mixture comprising (a) fuel; (b) a compound characterized by Formula I; and (c) a heavy compound, wherein the heavy compound comprises a compound of Formula I having at least one atom replaced with an isotope tag. As will be appreciated by one of skill in the art, and with the help of this disclosure, MS can easily distinguish between different isotopes of a given element, since MS separates and detects ions of slightly different masses, such as for example isotopes having a mass-to-charge ratio differing by ±1 or more.

Generally, differences in mass among isotopes of an element are very small, and the less abundant isotopes of an element are typically very rare. As such, if an isotope tag as disclosed herein is present in a compound, the signal of the isotope tag will be greater than the natural abundance of such isotope, making it possible to identify the heavy compound comprising the isotope tag. As will be appreciated by one of skill in the art, and with the help of this disclosure, the compound characterized by Formula I, and the heavy compound, wherein the heavy compound comprises a compound of Formula I having at least one atom replaced with an isotope tag, elute simultaneously or nearly simultaneously in the GC, and are analyzed simultaneously or nearly simultaneously on MS.

In an embodiment, the compound characterized by Formula I and the heavy compound comprising a compound of Formula I having at least one atom replaced with an isotope tag can each display MS peaks that are different (e.g., distinct, dissimilar, etc.) from each other, thereby enabling simultaneous detection of both the compound characterized by Formula I and the heavy compound.

Further, as will be appreciated by one of skill in the art, and with the help of this disclosure, the abundance of each peak corresponds to the amount of the compound that gave rise to that particular peak.

In an embodiment, the base peak of a heavy compound characterized by Formula I can comprise at least one isotope tag. In some embodiments, the base peak of a heavy compound characterized by Formula I can comprise all isotope tags of the heavy compound characterized by Formula I. In an embodiment, the molecular ion peak of a heavy compound characterized by Formula I can comprise at least one isotope tag. In some embodiments, the molecular ion peak of a heavy compound characterized by Formula I can comprise all isotope tags of the heavy compound characterized by Formula I.

In an embodiment, a method of determining adulteration of a fuel can comprise (i) acquiring a fuel sample; (ii) subjecting the fuel sample to $^{13}C$ NMR spectroscopy to yield $^{13}C$ NMR data; and (iii) comparing the $^{13}C$ NMR data of the fuel sample with the $^{13}C$ NMR data of the marked fuel composition (e.g., control data of the marked fuel composition). In such an embodiment, the method can further comprise determining an amount of the compound characterized by Formula I present in the composition and the fuel sample based on the $^{13}C$ NMR data. NMR spectroscopy is a research technique that exploits the magnetic properties of certain atomic nuclei, such as for example hydrogen ($^{1}H$ NMR) or carbon ($^{13}C$ NMR). Generally, NMR spectroscopy relies on the phenomenon of nuclear magnetic resonance and can provide detailed information about the structure, dynamics, reaction state, and chemical environment of molecules. The intramolecular magnetic field around an atom in a molecule changes the resonance frequency, thus giving access to details of the electronic structure of a molecule.

In an embodiment, a method of determining adulteration of a fuel can comprise subjecting to $^{13}C$ NMR spectroscopy a marked fuel mixture comprising (a) a fuel; (b) a compound characterized by Formula I; and (c) a heavy compound, wherein the heavy compound comprises a compound of Formula I having at least one atom replaced with an isotope tag, wherein the isotope tag comprises carbon-13 ($^{13}C$).

In an embodiment, a method of determining adulteration of a fuel can comprise (i) acquiring a fuel sample; (ii) subjecting the fuel sample to surface enhanced Raman scattering spectroscopy (SERS) to yield SERS data; and (iii) comparing the SERS data of the fuel sample with the SERS data of the marked fuel composition (e.g., control data of the marked fuel composition). In such an embodiment, the fuel sample can further be a marked fuel mixture. Raman spectroscopy is a technique used to observe vibrational, rotational, and other low-frequency modes in a molecule, which renders it sensitive to isotopic substitution, due to low-frequency modes in a molecule being influenced by the weight of the individual atoms in the bonds that lead to those modes. Generally, SERS is a surface-sensitive technique that enhances Raman scattering by molecules adsorbed on rough metal surfaces or by nanostructures such as plasmonic-magnetic silica nanotubes. SERS can also be performed in colloidal solutions. SERS is an extremely sensitive analytical technique and it has the potential of detecting single molecules.

In an embodiment, a method of determining adulteration of a fuel can comprise subjecting to SERS a marked fuel mixture comprising (a) a fuel; (b) a compound characterized by Formula I; and (c) a heavy compound, wherein the heavy compound comprises a compound of Formula I having at least one atom replaced with an isotope tag.

In some embodiments, determining adulteration of a fuel can be complicated by matrix effects. Generally, a "matrix" refers to an environment surrounding an analyte of interest (e.g., fuel marker), such as for example fuel components, solvent, laundering agents, masking agents, etc. In some cases, the matrix can influence the result of detecting a particular analyte, by interfering with the detection, an such interference can be referred for purposes of the disclosure herein as "matrix effect(s)." In some cases, matrix components can enhance transfer of analytes (e.g., fuel markers) through GC (matrix induced response enhancement); in other cases, matrix components can decrease analyte responses (matrix induced diminishment). For purposes of the disclosure herein, the term "matrix effects" encompasses the many different root causes of error that can occur in GC-based or GC-MS-based analyses as a result of matrix related issues.

A conventional calibration process for a routine GC/MS analysis can generally involve creating a series of accurately prepared samples ("calibration standards") containing known but varying concentrations of an analyte of interest (e.g., fuel marker) in a suitable and readily available solvent. The calibration standards can then be analyzed by GC-MS and a calibration curve can be generated by plotting an analyte response vs. a concentration of the analyte in the sample. Conventionally, the concentration of analyte in unknown samples can be determined by analyzing the unknown samples with the same methodology as the calibration standards, followed by using the measured analyte response to mathematically derive the concentration of the analyte in the unknown sample from the relationship described by the calibration curve. An increased accuracy of analyte detection (e.g., accurate analyte quantitation) in GC-MS can be achieved when a solvent used to create the calibration standards is closely matched to the matrix of the unknown samples. For example, isolating an analyte from a matrix can involve a step of extracting the analyte from an aqueous solution into an organic solvent, such as for example dichloromethane; it is likely that the most accurate quantitation for the analyte could be achieved by using a "matrix matched standard" method, wherein the calibration standards are prepared in the same organic solvent (e.g., dichloromethane). However, in some instances, even matching the matrix (e.g., matching a predominant solvent environment around an analyte) can be insufficient to achieve a desired level of analytical performance. In such instances, decreased analytical performance can manifest as matrix effects (e.g., inaccurate quantitation, decreased method ruggedness, low analyte detectability, reporting of false positives or negative results, etc.).

In some embodiments, a method of determining adulteration of a fuel can comprise subjecting a fuel sample to a method of separating at least a portion of the fuel marker from at least a portion of its fuel sample matrix by using any suitable methodology, such as for example solid phase extraction (SPE). Matrix effects can interfere in analysis of GC-MS-based markers in fuels during fuel authentication, e.g., can prevent an accurate quantitation of fuel markers by GC-MS. For example, matrix effects can be problematic in fuel authentication analyses in areas or countries where fuel composition varies greatly as a result of such areas or countries using more than one fuel stream source, wherein the fuel specifications and/or compositions are different for at least two of the fuel stream sources, due to such areas or countries only refining a portion of their fuel used internally; such areas or countries purchasing a portion of their fuel from outside suppliers; etc. Matrix effects can be greatly exacerbated by the fact that many real world samples (which can be of unknown pedigree) can be (and often are) adulterated with other substances (e.g., adulterants, laundering agents, etc.), such as other fuels types, industrial solvents, used oils, and the like, or combinations thereof. Fuel adulteration is generally unknown prior to a fuel authentication analysis, and since the existence of adulterants can be unknown, appropriate instrument calibration and generating a reliable calibration curve cannot be done under conventional methodologies.

In an embodiment, a method of determining adulteration of a fuel can further comprise subjecting a fuel sample (e.g., crude oil, asphalt mixes, diesel fuel, etc.) to SPE. Generally, SPE is a sample preparation technique that uses solid particles (e.g., chromatographic packing material) usually contained in a cartridge type device (e.g., SPE column), to chemically separate the different components of a sample, wherein samples are most often in a liquid state. The different components of a sample would generally elute in different fractions off the SPE column. SPE is commonly used for removal of interferences from samples to facilitate subsequent analysis of such samples.

In some embodiments, a fuel (e.g., fuel sample, marked fuel mixture, etc.) can comprise a matrix, wherein the matrix can comprise a non-interfering portion of the matrix (e.g., non-interfering components of the matrix) and an interfering portion of the matrix (e.g., interfering components of the matrix). The matrix generally refers to an environment surrounding the fuel marker and/or the heavy compound, as previously disclosed herein. In some embodiments, the interfering portion of the matrix can comprise masking agents. Generally, a masking agent refers to any agent (e.g., compound, substance, etc.) intentionally added to a fuel with the purpose of interfering with authenticating the fuel, e.g., with the purpose of interfering with accurately detecting the presence and amount (e.g., concentration) of markers (e.g., fuel markers) in the fuel. Nonlimiting examples of masking agents include any substance not native to the fuel, such as crude oil, used oil, solvents, other chemicals, and the like, or combinations thereof.

In an embodiment, a method of determining adulteration of a fuel can comprise (i) contacting a fuel sample with a heavy compound to form a marked fuel mixture, wherein the fuel sample comprises a fuel and a compound characterized by Formula I (e.g., fuel marker), and wherein the heavy compound comprises the compound of Formula I having at least one atom replaced with an isotope tag; (ii) subjecting the marked fuel mixture to SPE to yield a marked fuel mixture fraction, wherein at least a portion of the fuel marker and at least a portion of the heavy compound elute together in the marked fuel mixture fraction; and (iii) subjecting to an analytical technique the marked fuel mixture fraction to determine fuel adulteration. In such an embodiment, the marked fuel mixture can comprise a non-interfering portion of the matrix, interfering components of the matrix, the compound characterized by Formula I, and the heavy compound. SPE can separate at least a portion of interfering components of the matrix from the compound characterized by Formula I and the heavy compound, to yield a marked fuel mixture fraction comprising the compound characterized by Formula I and the heavy compound, wherein a concentration of the interfering components of the matrix in the marked fuel mixture fraction can be reduced by equal to or greater than about 75%, alternatively greater than about 80%, alternatively greater than about 85%, alternatively greater than about 90%, or alternatively greater than about 95%, when compared to a concentration of the interfering components of the matrix in the marked fuel mixture. Interfering compounds that might be present in the marked fuel mixture (e.g., masking agents, laundering agents, etc.) can be removed by SPE, and as such the fraction containing the fuel marker and the heavy compound can be further analyzed by any suitable analytical technique (e.g., GC-MS). Even if SPE removes some of the fuel marker and corresponding heavy compound from the marked fuel mixture, the ratio of fuel marker to heavy compound is expected to remain substantially the same, as both the marker and the corresponding heavy compound would be removed from the fuel sample to the same extent due to having the same chemical formula differing only by the isotope tag(s). Further, the ratio of fuel marker to corresponding heavy compound is expected to remain substantially the same even if the dilution (e.g., concentration) of the marker and the corresponding heavy compound changes in the marked fuel mixture fraction as compared to the marked fuel mixture. In some embodiments, the matrix comprises masking agents (e.g., interfering components of the matrix).

In an embodiment, a fuel can be dually marked (e.g., fuel sample can be marked with two different markers, wherein each marker can be characterized by Formula I). In such an embodiment, a dually marked fuel sample can be contacted with heavy compounds corresponding to the two different markers that mark the fuel to form a dually marked fuel mixture. The dually marked fuel mixture can be further subjected to SPE to obtain marked fuel mixture fractions, wherein each set of marker and corresponding heavy compound can elute in separate (e.g., different, distinct) fractions. Interfering compounds that might be present in the fuel sample (e.g., masking agents) can be removed by SPE, and as such the fractions containing each set of marker and corresponding heavy compound can be further analyzed by any suitable analytical technique (e.g., GC-MS). While the present disclosure discusses a method of determining adulteration of a dually marked fuel, it should be understood that such method or any steps thereof can be applied in a method of determining adulteration of a fuel marked with any suitable number of markers, such as for example three, four, five, six, seven, eight, nine, ten, or more markers.

In an embodiment, a method of determining adulteration of a fuel can further comprise contacting a fuel sample with a heavy compound to form a marked fuel mixture; subjecting the marked fuel mixture to SPE; recovering a marked fuel mixture fraction, wherein the fraction comprises a fuel marker and corresponding heavy compound, and wherein the fraction is substantially free of interfering compounds (e.g., masking agents) that could have been present in the fuel sample; and subjecting the marked fuel mixture fraction to GC-MS analysis as previously described herein.

In an embodiment, a method of determining adulteration of a fuel can further comprise contacting a dually marked fuel sample with corresponding heavy compounds to form a dually marked fuel mixture; subjecting the dually marked fuel mixture to SPE; recovering marked fuel mixture fractions, wherein separate fractions comprise each set of fuel marker and corresponding heavy compound, and wherein such fractions are substantially free of interfering compounds (e.g., masking agents) that could have been present in the fuel sample; and subjecting the marked fuel mixture fractions to GC-MS analysis as previously described herein.

In an embodiment, a fuel marker can comprise a compound characterized by Formula I:

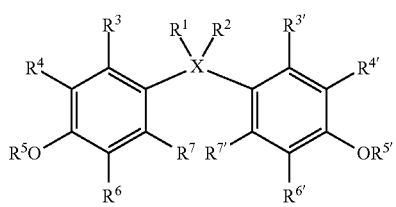

Formula I wherein X can be carbon (C), oxygen (O), or sulfur (S); $R^1$ and $R^2$ can each independently be hydrogen, a $C_1$ to $C_7$ alkyl group, or a phenyl group; $R^3$ and $R^{3'}$ can each independently be hydrogen or a methyl group; $R^4$ and $R^{4'}$ can each independently be hydrogen, a methyl group, a tert-butyl group, a cyclohexyl group, or a phenyl group; $R^5$ and $R^{5'}$ can each independently be a $C_6$ or a $C_7$ alkyl group; $R^6$ and $R^{6'}$ can each independently be hydrogen or a $C_1$ to $C_4$ alkyl group; and $R^7$ and $R^{7'}$ can each independently be hydrogen or a methyl group; and wherein the compound characterized by Formula I when subjected to GC-MS using electron ionization can produce at least one ion having a mass-to-charge ratio of greater than about 300 at an ionization energy of equal to or greater than about 70 eV.

In an embodiment, a method of forming a marked fuel composition can comprise contacting (a) a fuel and (b) at least one compound characterized by Formula I:

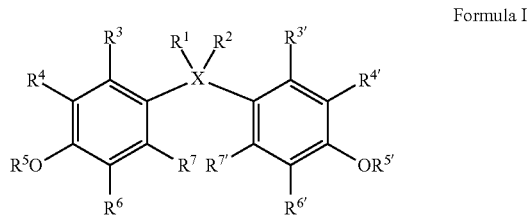

Formula I wherein X can be carbon (C), oxygen (O), or sulfur (S); $R^1$ and $R^2$ can each independently be hydrogen, a $C_1$ to $C_7$ alkyl group, or a phenyl group; $R^3$ and $R^{3'}$ can each independently be hydrogen or a methyl group; $R^4$ and $R^{4'}$ can each independently be hydrogen, a methyl group, a tert-butyl group, a cyclohexyl group, or a phenyl group; $R^5$ and $R^{5'}$ can each independently be a $C_6$ or a $C_7$ alkyl group; $R^6$ and $R^{6'}$ can each independently be hydrogen or a $C_1$ to $C_4$ alkyl group; and $R^7$ and $R^{7'}$ can each independently be hydrogen or a methyl group; and wherein the compound characterized by Formula I when subjected to GC-MS using electron ionization can produce at least one ion having a mass-to-charge ratio of greater than about 300 at an ionization energy of equal to or greater than about 70 eV.

In an embodiment, a method of determining adulteration of a fuel can comprise subjecting to GC-MS a marked fuel composition comprising (a) a fuel and (b) at least one compound characterized by Formula I:

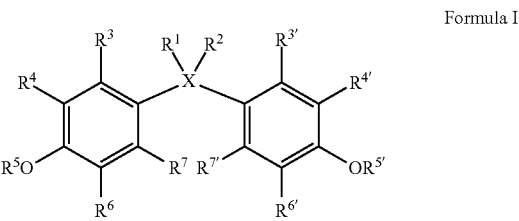

Formula I wherein X can be carbon (C), oxygen (O), or sulfur (S); $R^1$ and $R^2$ can each independently be hydrogen, a $C_1$ to $C_7$ alkyl group, or a phenyl group; $R^3$ and $R^{3'}$ can each independently be hydrogen or a methyl group; $R^4$ and $R^{4'}$ can each independently be hydrogen, a methyl group, a tert-butyl group, a cyclohexyl group, or a phenyl group; $R^5$ and $R^{5'}$ can each independently be a $C_6$ or a $C_7$ alkyl group; $R^6$ and $R^{6'}$ can each independently be hydrogen or a $C_1$ to $C_4$ alkyl group; and $R^7$ and $R^{7'}$ can each independently be hydrogen or a methyl group; and wherein the compound characterized by Formula I when subjected to GC-MS using electron ionization can produce at least one ion having a mass-to-charge ratio of greater than about 300 at an ionization energy of equal to or greater than about 70 eV.

In an embodiment, a method of determining adulteration of a fuel can comprise subjecting to GC-MS a marked fuel mixture comprising (a) a fuel; (b) a compound characterized by Formula I:

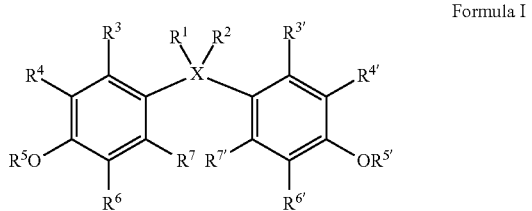

Formula I wherein X can be carbon (C), oxygen (O), or sulfur (S); $R^1$ and $R^2$ can each independently be hydrogen, a $C_1$ to $C_7$ alkyl group, or a phenyl group; $R^3$ and $R^{3'}$ can each independently be hydrogen or a methyl group; $R^4$ and $R^{4'}$ can each independently be hydrogen, a methyl group, a tert-butyl group, a cyclohexyl group, or a phenyl group; $R^5$ and $R^{5'}$ can each independently be a $C_6$ or a $C_7$ alkyl group; $R^6$ and $R^{6'}$ can each independently be hydrogen or a $C_1$ to $C_4$ alkyl group; and $R^7$ and $R^{7'}$ can each independently be hydrogen or a methyl group; and (c) and a heavy compound, wherein the heavy compound comprises a compound of Formula I having at least one atom replaced with an isotope tag, alternatively a plurality of the atoms are isotopically substituted. In such an embodiment, the isotope tag comprises deuterium ($^2H$).

In an embodiment, a method of determining adulteration of a fuel can comprise (i) contacting a fuel sample with a heavy compound to form a marked fuel mixture, wherein the fuel sample comprises a fuel and a compound characterized by Formula I:

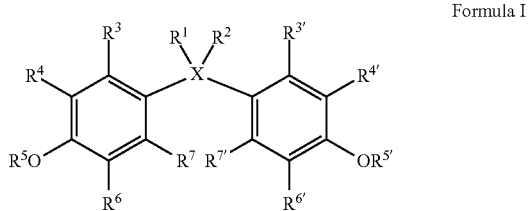

Formula I wherein X can be carbon (C), oxygen (O), or sulfur (S); $R^1$ and $R^2$ can each independently be hydrogen, a $C_1$ to $C_{20}$ alkyl group, or a $C_6$ to $C_{10}$ aryl group; $R^3$ and $R^{3'}$ can each independently be hydrogen or a $C_1$ to $C_4$ alkyl group; $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group; $R^5$ and $R^{5'}$ can each independently be a $C_4$ to $C_{10}$ alkyl group; $R^6$ and $R^{6'}$ can each independently be hydrogen or a $C_1$ to $C_6$ alkyl group; and $R^7$ and $R^{7'}$ can each independently be hydrogen or a $C_1$ to $C_4$ alkyl group; and wherein the heavy compound comprises the compound of Formula I having at least one atom replaced with deuterium; (ii) subjecting the marked fuel mixture to solid phase extraction (SPE) to yield a marked fuel mixture fraction, wherein at least a portion of the compound characterized by Formula I and at least a portion of the heavy compound elute together in the marked fuel mixture fraction; and (iii) subjecting to gas chromatography-mass spectrometry (GC-MS) the marked fuel mixture fraction to determine fuel adulteration, wherein each of the compound characterized by Formula I and the heavy compound when subjected to GC-MS using electron ionization produces at least one ion having a mass-to-charge ratio of from about 300 to about 600 at an ionization energy of equal to or greater than about 70 eV. In such an embodiment, the compound characterized by Formula I can have Structure F:

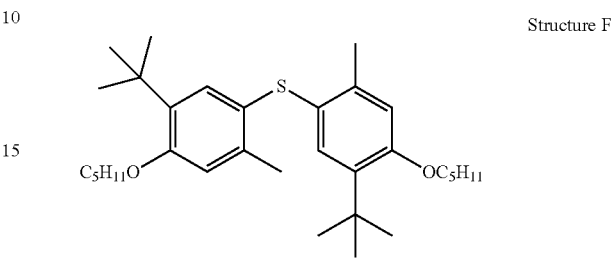

Structure F and the heavy compound can have d-Structure F:

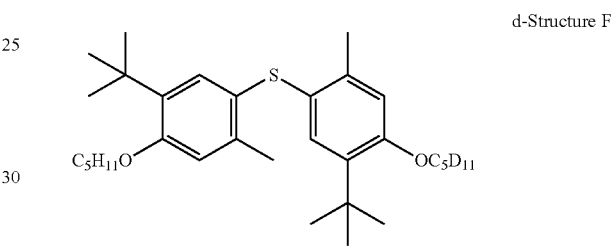

d-Structure F

In an embodiment, the marked fuel compositions as disclosed herein advantageously display improvements in one or more characteristics, when compared to similar compositions lacking a fuel marker as disclosed herein. For example, the marked fuel compositions can advantageously display enhanced detectability, e.g., a lower amount of fuel marker can be used to mark fuel compositions and enable determining the fuel adulteration.

In an embodiment, the fuel markers as disclosed herein cannot be extracted (e.g., removed, taken out, etc.) from a marked fuel composition by conventional means. For example, the fuel marker cannot be substantially differentially adsorbed from a marked fuel composition using conventional inexpensive adsorbents; cannot be removed by extraction with acids, bases, or immiscible solvents; cannot be easily oxidized, reduced or reacted with common reagents to effectively remove the fuel marker; and the like. Further, it should be difficult (e.g., not practical, not feasible financially) to disguise the presence of the fuel marker by masking the marker via reactions with masking agents.

In an embodiment, the fuel markers as disclosed herein should not alter (e.g., modify, change, interfere with, etc.) the properties of the fuel. In an embodiment, the fuel markers as disclosed herein can be advantageously stable under conditions (e.g., environmental conditions) that the fuel can be subjected to.

In an embodiment, the fuel markers as disclosed herein can advantageously display an adequate solubility in solvents for marker delivery. For example, the fuel markers can be characterized by a solubility in solvents of equal to or greater than about 50%, alternatively from about 50% to about 20%, or alternatively from about 20% to about 5% at 25° C.

In an embodiment, the fuel markers as disclosed herein can advantageously allow qualitative and/or quantitative authentication of fuels, such as for example by GC-MS analysis. In an embodiment, the fuel markers as disclosed herein can advantageously allow for the use of small amounts (e.g., from about 1 ppb to about 50 ppm, based on the total weight of the marked fuel composition) of fuel markers as compared to other conventional markers.

In an embodiment, the fuel markers as disclosed herein can allow for using and detecting more than one marker simultaneously, such as for example by GC-MS. In such an embodiment, authentication of a fuel can be accomplished by comparing more than one variable, e.g., by simultaneously detecting the presence and/or concentration of more than one fuel marker by GC-MS, for example.

In an embodiment, fuel markers and methods of using same as disclosed herein can advantageously mitigate matrix effects. Conventional analytical methods (e.g., matrix matched standard-based calibrations with bracketing standards) for analyzing fuel markers cannot accurately quantify markers in refined petroleum products (e.g., fuels). In an embodiment, a method of using the fuel markers to determine fuel adulteration as disclosed herein can advantageously display improved detection accuracy, without adding substantial sample preparation steps (which can be both costly and time consuming), when compared to conventional detection methods. Additional advantages of the marked fuel compositions and methods of producing and using same as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The compound characterized by Structure F (i.e., bis(5-(tert-butyl)-2-methyl-4-(pentyloxy)phenyl)sulfane) was synthesized by reaction of 4,4'-thiobis(2-(tert-butyl)-5-methylphenol) (4,4'-thiobis(6-tert-butyl-m-cresol)) with 1-bromopentane, according to the following reaction scheme:

Structure F

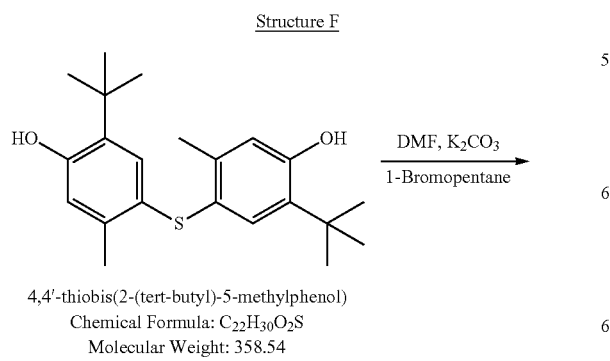

4,4'-thiobis(2-(tert-butyl)-5-methylphenol)
Chemical Formula: C$_{22}$H$_{30}$O$_2$S
Molecular Weight: 358.54

-continued

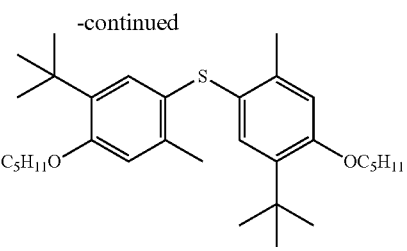

bis(5-(tert-butyl)-2-methyl-4-(pentyloxy)phenyl)sulfane
Chemical Formula: C$_{32}$H$_{50}$O$_2$S
Molecular Weight: 498.81

4,4'-thiobis(2-(tert-butyl)-5-methylphenol) (4,4'-thiobis(6-tert-butyl-m-cresol)) (1 equivalent (eq), 10 g, 27.89 mmol), potassium carbonate (2.5 eq, 9.6363 g, 69.725 mmol, 138.205 g/mol), and 1-bromopentane (2.1 eq, 8.8463 g, 7.3 mL, 58.569 mmol, 151.04 g/mol, d=1.218 g/mL) were dissolved in N,N-dimethylformamide (DMF, 90 mL) at 90° C. The reaction was stirred until complete as determined by thin layer chromatography (TLC). The reaction was poured into water and extracted with ethyl acetate. The aqueous layer was discarded and the ethyl acetate was back-extracted three times with brine to remove residual DMF. The resulting organic solution was dried with magnesium sulfate, filtered, and concentrated on a rotary evaporator. The crude product was recrystallized from methanol, filtered, and then washed with cold methanol. The product was dried at 50° C. under high vacuum for 12 hours to yield a fine white powder (compound characterized by Structure F: bis(5-(tert-butyl)-2-methyl-4-(pentyloxy)phenyl)sulfane). The yield was 8.4211 g (60.5%).

Example 2

The compound characterized by Structure B (i.e., bis(4-(heptyloxy)phenyl)sulfane) was synthesized by reaction of 4,4'-thiodiphenol (bis(4-hydroxyphenyl)sulfide) with 1-bromoheptane, according to the following reaction scheme:

Structure B

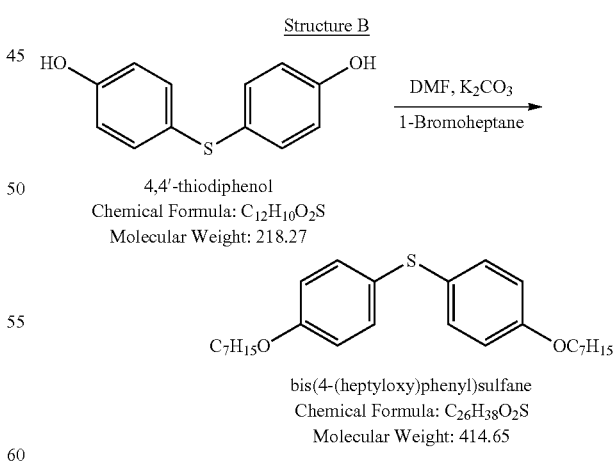

4,4'-thiodiphenol
Chemical Formula: C$_{12}$H$_{10}$O$_2$S
Molecular Weight: 218.27 bis(4-(heptyloxy)phenyl)sulfane
Chemical Formula: C$_{26}$H$_{38}$O$_2$S
Molecular Weight: 414.65

4,4'-thiodiphenol (bis(4-hydroxyphenyl) sulfide) (1 eq, 10 g, 45.8 mmol), potassium carbonate (2.5 eq, 15.8245 g, 114.5 mmol, 138.205 g/mol), and 1-bromoheptane (2.5 eq, 20.5070 g, 18 mL, 114.5 mmol, 179.10 g/mol, d=1.14 g/mL) were dissolved in DMF (100 mL) at 80° C. The reaction was stirred until complete as determined by TLC. The reaction was poured into water and extracted with dichloromethane (DCM). The aqueous layer was discarded and the DCM was back-extracted three times to remove residual DMF. The resulting organic solution was dried with sodium sulfate, filtered, and concentrated on a rotary evaporator. The product was recrystallized from ethanol, filtered, and then washed with cold ethanol. The product was subsequently put through a silica plug with 50-50 hexanes-DCM and concentrated on a rotary evaporator to yield a white powder (compound characterized by Structure B: bis(4-(heptyloxy) phenyl)sulfane). The product was dried under high vacuum for 24 hours at 50° C. to remove residual solvents and 1-bromoheptane. The yield was 5 g (26.3%)

Example 3

The compound characterized by Structure C (i.e., bis(4-(heptyloxy)-3-methylphenyl)sulfane) was synthesized by reaction of 4,4'-thiobis(2-methylphenol) (bis(4-hydroxy-3-methylphenyl) sulfide) with 1-bromoheptane, according to the following reaction scheme:

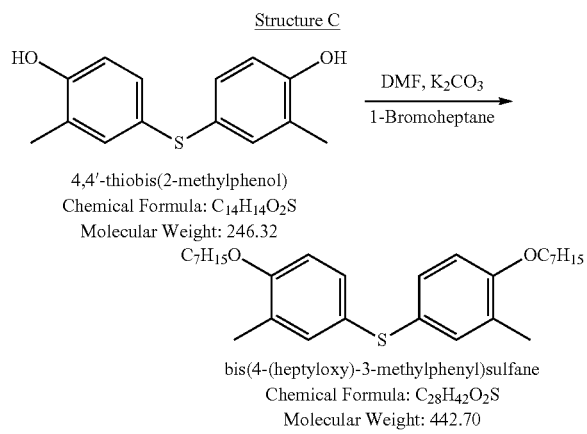

4,4'-thiobis(2-methylphenol)
Chemical Formula: $C_{14}H_{14}O_2S$
Molecular Weight: 246.32 bis(4-(heptyloxy)-3-methylphenyl)sulfane
Chemical Formula: $C_{28}H_{42}O_2S$
Molecular Weight: 442.70

4,4'-thiobis(2-methylphenol) (bis(4-hydroxy-3-methylphenyl) sulfide) (1 eq, 10 g, 40.6 mmol), potassium carbonate (3.0 eq, 16.8334 g, 121.8 mmol, 138.205 g/mol), and 1-bromoheptane (3 eq, g, 21.8144 g, 19.2 mL, 121.8 mmol, 179.10 g/mol, d=1.14 g/mL) were dissolved in DMF (150 mL) at 80° C. The reaction was stirred until complete as determined by TLC. The reaction was poured into water and extracted with ethyl acetate. The aqueous layer was discarded and the ethyl acetate was back-extracted three times to remove residual DMF. The resulting organic solution was dried with sodium sulfate, filtered, and concentrated on a rotary evaporator. The product was recrystallized from ethanol, filtered, and then washed with cold ethanol. The product (compound characterized by Structure C: bis(4-(heptyloxy)-3-methylphenyl)sulfane) was dried at 50° C. under high vacuum for 24 hours to remove residual 1-bromoheptane. The yield was 9.9320 g (55.3%).

Example 4

The compound characterized by Structure A (i.e., 4,4'-oxybis((heptyloxy)benzene)) was synthesized by reaction of 4,4'-oxydiphenol (4,4'-dihydroxydiphenyl ether) with 1-bromopentane, according to the following reaction scheme:

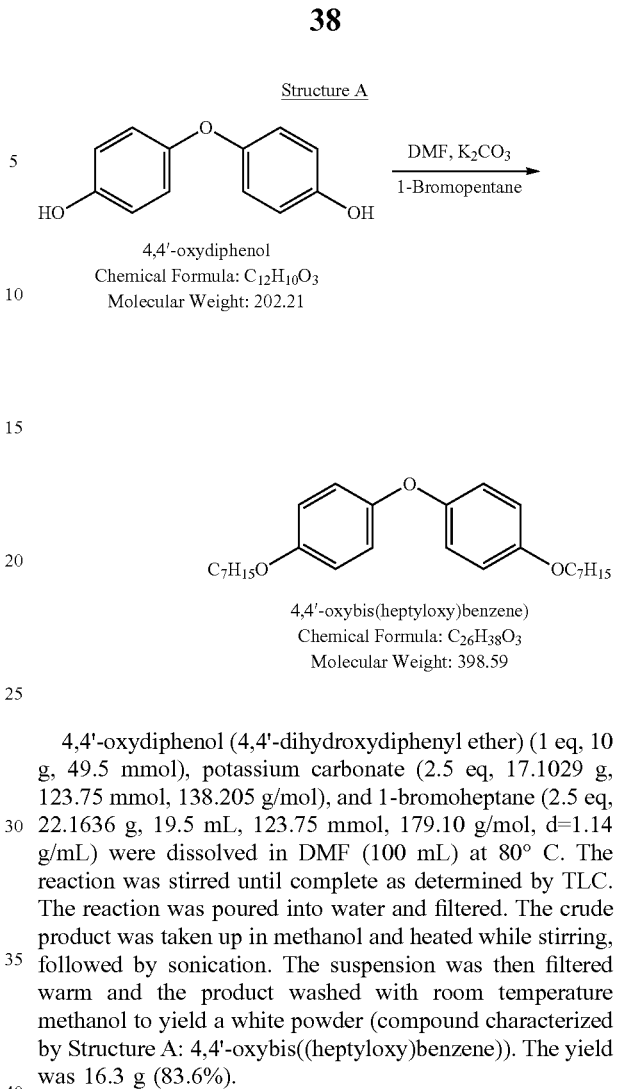

Structure A 4,4'-oxydiphenol
Chemical Formula: $C_{12}H_{10}O_3$
Molecular Weight: 202.21

4,4'-oxybis(heptyloxy)benzene)
Chemical Formula: $C_{26}H_{38}O_3$
Molecular Weight: 398.59

4,4'-oxydiphenol (4,4'-dihydroxydiphenyl ether) (1 eq, 10 g, 49.5 mmol), potassium carbonate (2.5 eq, 17.1029 g, 123.75 mmol, 138.205 g/mol), and 1-bromoheptane (2.5 eq, 22.1636 g, 19.5 mL, 123.75 mmol, 179.10 g/mol, d=1.14 g/mL) were dissolved in DMF (100 mL) at 80° C. The reaction was stirred until complete as determined by TLC. The reaction was poured into water and filtered. The crude product was taken up in methanol and heated while stirring, followed by sonication. The suspension was then filtered warm and the product washed with room temperature methanol to yield a white powder (compound characterized by Structure A: 4,4'-oxybis((heptyloxy)benzene)). The yield was 16.3 g (83.6%).

Example 5

A deuterated compound characterized by Structure F, d-Structure F (i.e., bis(5-(tert-butyl)-2-methyl-4-(pentyl-$d_{22}$-oxy)phenyl)sulfane) was synthesized by reaction of 4,4'-thiobis(2-(tert-butyl)-5-methylphenol) (4,4'-thiobis(6-tert-butyl-m-cresol)) with deuterated 1-bromopentane (1-bromopentane-$d_{11}$), according to the following reaction scheme:

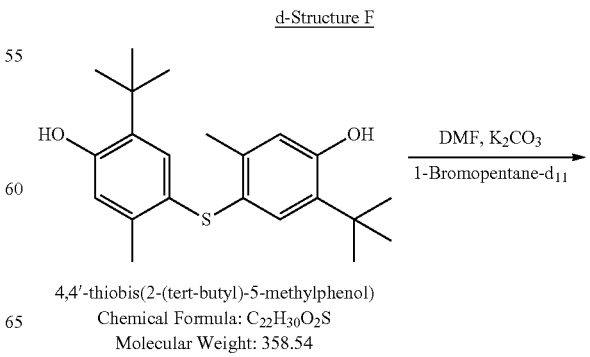

d-Structure F 4,4'-thiobis(2-(tert-butyl)-5-methylphenol)
Chemical Formula: $C_{22}H_{30}O_2S$
Molecular Weight: 358.54

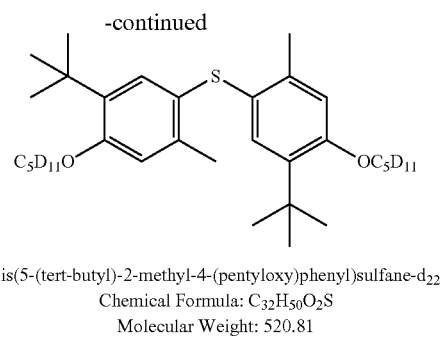

bis(5-(tert-butyl)-2-methyl-4-(pentyloxy)phenyl)sulfane-d$_{22}$
Chemical Formula: C$_{32}$H$_{50}$O$_2$S
Molecular Weight: 520.81

4,4'-thiobis(2-(tert-butyl)-5-methylphenol) (4,4'-thiobis (6-tert-butyl-m-cresol)) (1 eq, 1.1641 g, 3.2467 mmol), potassium carbonate (2.1 eq, 0.9423 g, 6.8181 mmol, 138.205 g/mol), and 1-bromopentane-d$_{11}$ (1.9 eq, 1 g, 6.1687 mmol, 162.11 g/mol) were dissolved in 10 mL DMF at 85° C. The reaction was stirred until complete as determined by TLC. The reaction was poured into water and extracted with DCM. The aqueous layer was discarded and the DCM was back-extracted three times to remove residual DMF. The resulting organic solution was dried with sodium sulfate, filtered, and concentrated on a rotary evaporator. The product was subsequently put through a silica plug with 50-50 hexanes-DCM and concentrated on a rotary evaporator. The product (deuterated compound characterized by Structure F, d-Structure F: bis(5-(tert-butyl)-2-methyl-4-(pentyl-d$_{22}$-oxy)phenyl)sulfane) was dried under high vacuum for 24 hours at 50° C. to remove residual 1-bromopentane. The yield was 1 g (59.1%).

Example 6

A deuterated compound characterized by Structure B, d-Structure B (i.e., bis(4-(heptyl-d$_{30}$-oxy)phenyl)sulfane) was synthesized by reaction of 4,4'-thiodiphenol (bis(4-hydroxyphenyl) sulfide) with deuterated 1-bromoheptane (1-bromoheptane-d$_5$), according to the following reaction scheme:

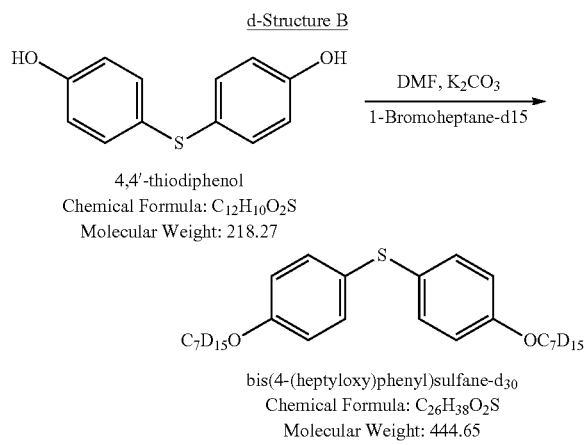

4,4'-thiodiphenol (bis(4-hydroxyphenyl) sulfide) (1 eq, 1.1832 g, 5.4 mmol), potassium carbonate (2.1 eq, 1.57 g, 11.4 mmol, 138.205 g/mol), and 1-bromoheptane-d$_5$ (1.9 eq, 2 g, 10.3 mmol, 194.19 g/mol) were dissolved in DMF (50 mL) at 85° C. The reaction was stirred until complete as determined by TLC. The reaction was poured into water and extracted with DCM. The aqueous layer was discarded and the DCM was back-extracted three times to remove residual DMF. The resulting organic solution was dried with sodium sulfate, filtered, and concentrated on a rotary evaporator. The product was recrystallized from ethanol, filtered, and then washed with cold ethanol. The product was subsequently put through a silica plug with 50-50 hexanes-DCM and concentrated on a rotary evaporator to yield a white powder (deuterated compound characterized by Structure B, d-Structure B: bis(4-(heptyl-d$_{30}$-oxy)phenyl)sulfane). The product was dried under high vacuum for 24 hours at 50° C. to remove residual solvents and 1-bromoheptane. The yield was 1.2 g (50%).

Example 7

The identity of fuel samples was investigated. More specifically, the concentration of fuel markers in various fuel samples was investigated.

Sample and Standard Preparation.

Internal standard solutions were prepared by accurately diluting the fuel sample and adding a heavy fuel marker as internal standard to each diluted sample. For fuel marking, a concentrate of fuel marker in toluene was prepared to a concentration of 50 ppm (m/v) and added to the diesel fuel to yield a final concentration of marker in diesel of 100 ppb (m/v).

Instrumentation.

GC-MS analyses were conducted on an Agilent 7890B Gas Chromatograph equipped with an Agilent 5977A Mass Selective Detector and an Agilent 7650 Automatic Liquid Sampler. A DB-35 ms Ultra Inert column (15 m×0.250 mm×0.25 μm) was connected directly to a split/splitless inlet and to the mass spectrometer, and a helium carrier was utilized. The method conditions for all analyses were as follows: constant flow of 1.5 mL/min, inlet temperature of 340° C., pulsed splitless injection at 40 psi for 0.5 min, temperature program at 150° C. for 0.5 min, then a 30° C./min ramp to 300° C. followed by a 20° C./min ramp to 340° C. (4 min hold), and a MS transfer line temperature of 340° C. MS quadrupole was operated in selected ion monitoring (SIM) mode with two ions being monitored for each analyte, and automated tuning was performed using the ETUNE parameter set.

For analysis, internal standard and sample were co-injected into the inlet via a 5 μL syringe as a sandwich injection where 1 μL of sample was co-injected with 0.5 μL of the internal standard solution. For samples in which the injection of no internal standard was desired, a sandwich injection was still performed so as to maintain the same analytical methodology for comparison purposes, only the internal standard solution was replaced by a sample of toluene.

GC-MS Analysis.

All samples were analyzed in triplicate and the three results averaged for reporting purposes. A bracketing standard of the marker in locally obtained diesel fuel was injected every fifth injection and used to calculate the concentrations of the 5 diesel fuel samples in the study.

Samples of diesel fuels (sample #1, sample #2, sample #3, sample #4, and sample #5) from various fuel stations across the globe were accurately marked with a compound characterized by Structure F at a concentration of 100 ppb (m/v). These samples were analyzed in triplicate and the resulting data are displayed in Table 1 (ISTD=internal standard characterized by d-Structure F) and FIG. 1.

TABLE 1

| Sample ID | ISTD Response | Fuel Marker Response | Calculated Fuel Marker Concentration (ppb) |
|---|---|---|---|
| Samples with ISTD | | | |
| Diesel Standard | 182,697 | 30,318 | — |
| Sample #5 | 143,764 | 25,061 | 105.8 |
| Sample #2 | 29,046 | 5,046 | 105.5 |
| Sample #1 | 69,070 | 13,265 | 116.6 |
| Sample #3 | 192,864 | 30,577 | 96.2 |
| Sample #4 | 175,005 | 29,966 | 103.9 |
| Diesel Standard | 180,052 | 29,843 | — |
| Sample #5 | 138,817 | 24,761 | 108.3 |
| Sample #2 | 28,689 | 4,818 | 101.9 |
| Sample #1 | 70,016 | 12,845 | 111.4 |
| Sample #3 | 190,001 | 30,702 | 98.1 |
| Sample #4 | 179,007 | 29,391 | 99.7 |
| Diesel Standard | 179,656 | 29,852 | — |
| Sample #5 | 142,773 | 24,382 | 103.7 |
| Sample #2 | 28,408 | 5,029 | 107.5 |
| Sample #1 | 69,699 | 13,002 | 113.2 |
| Sample #3 | 191,564 | 30,497 | 96.6 |
| Sample #4 | 179,568 | 29,387 | 99.3 |
| Diesel Standard | 178,788 | 29,810 | — |
| Samples without ISTD | | | |
| Diesel Standard | — | 30,663 | — |
| Sample #5 | — | 25,709 | 83.4 |
| Sample #2 | — | 5,115 | 16.6 |
| Sample #1 | — | 13,292 | 43.1 |
| Sample #3 | — | 31,964 | 103.7 |
| Sample #4 | — | 29,987 | 97.3 |
| Diesel Standard | — | 30,994 | — |
| Sample #5 | — | 25,500 | 82.7 |
| Sample #2 | — | 5,090 | 16.5 |
| Sample #1 | — | 13,353 | 43.3 |
| Sample #3 | — | 31,966 | 103.6 |
| Sample #4 | — | 30,169 | 97.8 |
| Diesel Standard | — | 30,711 | — |
| Sample #5 | — | 25,389 | 82.3 |
| Sample #2 | — | 5,109 | 16.6 |
| Sample #1 | — | 13,272 | 43.0 |
| Sample #3 | — | 31,470 | 102.0 |
| Sample #4 | — | 30,442 | 98.6 |
| Diesel Standard | — | 31,015 | — |

Figure 2:
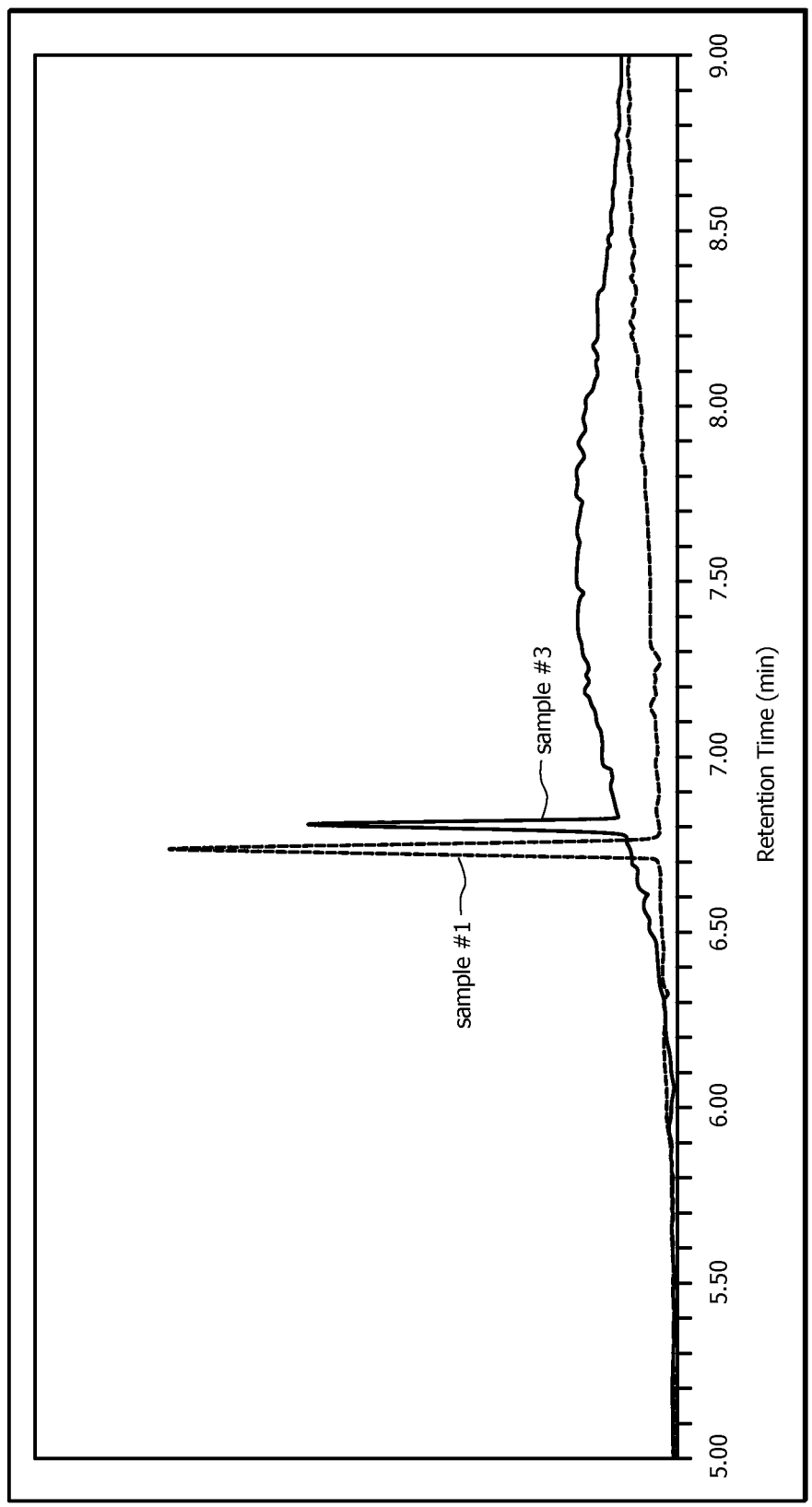
FIG. 2 displays ion chromatograms for fuel markers in different diesel fuel samples.

For the standard analysis, a standard sample of diesel fuel obtained locally (diesel standard) was marked with the compound characterized by Structure F at a concentration of 100 ppb (m/v) and run every fifth injection to serve as a bracketing standard. The average response from the bracketing standards were determined and used to calculate the concentration of marker in the different fuel samples. FIG. 2 displays extracted ion chromatograms (498.3 m/z) for sample #1 and sample #3. In sample #3, the suppression of the fuel marker is clearly evident as compared to sample #1, as area counts for the marker around 6.7 minutes are very different for the sample concentration of marker in both samples.

When the same samples were analyzed and a deuterated internal standard was added (via co-injection for this example), the calculated concentrations were far more accurate, as seen in Table 1 and FIG. 1. The average predicted value using conventional bracketing standard methodology was 69 ppb for the five diesel samples (sample #1, sample #2, sample #3, sample #4, and sample #5), whereas while using the internal standard methodology as described here, the average concentration for the five diesel samples was 104 ppb. The internal standard deuterated compound and the fuel marker being suppressed by the matrix to the same extent resulted in a dramatic improvement in accuracy. Therefore, by taking a ratio of responses of the fuel marker to internal standard (i.e., fuel marker response/internal standard response), instead of just the fuel marker response, the signal suppression can be mitigated and a much more accurate result can be determined.

Data Analysis.

The data was analyzed by using a conventional bracketing standard approach, wherein a standard sample (labeled herein "Diesel Standard") was a sample of diesel to which 100 ppb of marker (characterized by Structure F) has been added. During the analytical sequence, the "Diesel Standard" was injected prior to (e.g., preceding) and following (e.g., succeeding) the samples of unknown marker concentration. Generally, if a large number of samples of unknown marker concentration have to be analyzed, then a standard sample can be injected every 5-10 injections of samples of unknown marker concentration. In all cases, the standard sample was the same. In calculating the marker concentration of the samples (#1, #2, #3, #4, #5, etc.), the response of the marker in the standard injections surrounding (or bracketing: preceding, succeeding, etc.) the samples was averaged and the response of each sample was divided by the average response of the standard sample (e.g., the bracketing standard) and multiplied by the concentration of the marker in the standard sample according to equation (1):

$$C_x = 2 \times \frac{R_x}{(R_{Std\,1} + R_{Std\,2})} \times C_{Std} \quad (1)$$

wherein $C_x$=concentration of the marker in sample X of unknown marker concentration; wherein $R_x$=marker response in the sample X of unknown marker concentration; wherein $R_{Std\,1}$=marker response of the standard sample preceding the sample X of unknown marker concentration; wherein $R_{Std\,2}$=marker response of the standard sample succeeding the sample X of unknown marker concentration; wherein $C_{Std}$=concentration of the marker in the standard sample; and wherein $R_{Std\,1}$ and $R_{Std\,2}$ are different injections of the same standard sample having a marker concentration of $C_{Std}$. For purposes of the disclosure herein, "response" refers to the magnitude of the analytical signal or response. Similarly, the concentration of the marker in fuel samples can be calculated by utilizing the ISTD as described herein, according to equation (2):

$$C_x = 2 \times \frac{RR_x}{(RR_{Std\,1} + RR_{Std\,2})} \times C_{Std} \quad (2)$$

wherein $C_x$=concentration of the marker in sample X of unknown marker concentration; wherein $RR_x$=marker response ratio, or marker response/ISTD response for sample X of unknown marker concentration; wherein $RR_{Std\,1}$=marker response ratio, or marker response/ISTD response of the standard sample preceding the sample X of unknown marker concentration; wherein $RR_{Std\,2}$=marker response ratio, or marker response/ISTD response of the standard sample succeeding the sample X of unknown marker concentration; wherein $C_{Std}$=concentration of the marker in the standard sample; and wherein $R_{Std\,1}$ and $R_{Std\,2}$ are different injections of the same standard sample having a marker concentration of $C_{Std}$. As will be appreciated by one of skill in the art, and with the help of this disclosure, while the concentrations were calculated herein by using a single point calibration for simplicity, the principles of marker to internal standard response ratios can be applied to any multipoint calibration curve or calibration process to enhance the accuracy of the calculated marker concentration.

It is noteworthy from the data collected (Table 1, FIGS. 1 and 2) that even using a matrix matched standard gave very poor accuracy when analyzing diesel samples of different origin. These data speak to the fact that diesel fuel, and virtually all hydrocarbon-based fuels can be highly variable in nature. The source of the crude oil, refining conditions, age, and environmental storage conditions all have a dramatic impact on the chemical composition of the fuel. Further, these differences can have a significant impact on the analysis of chemical fuel markers added to fuels to aide in their identification/authentication.

Example 8

The identity of fuel samples was investigated. More specifically, the concentration of fuel markers in various fuel samples was investigated prior to and subsequent to solid phase extraction (SPE). Fuel samples and analysis were prepared and conducted as described in Example 7.

Samples were acquired and marked with a compound characterized by Structure F as described in Example 7. Sample #1, sample #2, and sample #5 of Example 7 were analyzed prior to and subsequent to SPE. Upon SPE, the samples were labeled sample #1a, sample #2a, and sample #5a, respectively. For SPE analysis, a solution of ISTD (characterized by d-Structure F) in hexane (3 mL) (e.g., ISTD hexane solution) was added to 0.225 mL of the fuel sample of unknown marker concentration to form an unknown sample in ISTD hexane solution, which was mixed to ensure complete dissolution. A 1 g silica gel SPE cartridge was conditioned with 5 mL of hexane prior to the addition of 2 mL of the unknown sample in ISTD hexane solution. After the entire unknown sample in ISTD hexane solution passed through the SPE column, the SPE column was rinsed with 16 mL of hexane to remove interferences from the sample of unknown marker concentration. The ISTD and marker were then eluted from the SPE column with 2 mL of toluene into a vial which was then analyzed directly via GC-MS.

All samples were analyzed in triplicate and the resulting data are displayed in Table 2 (ISTD=internal standard characterized by d-Structure F).

TABLE 2

| Sample ID | ISTD Response | Fuel Marker Response | Calculated Fuel Marker Concentration (ppb) |
|---|---|---|---|
| Samples Post-SPE Cleanup | | | |
| Diesel Standard | 75,700 | 2,227 | — |
| Sample #5a | 118,209 | 3841 | 96.5 |
| Sample #2a | 128,047 | 4491 | 104.1 |
| Sample #1a | 130,170 | 4530 | 103.3 |
| Diesel Standard | 84,104 | 2,474 | — |
| Sample #5a | 120,835 | 3,976 | 97.7 |
| Sample #2a | 129,746 | 4,606 | 105.4 |
| Sample #1a | 128,500 | 4,506 | 104.1 |
| Diesel Standard | 88,641 | 2,667 | — |
| Sample #5a | 134,858 | 4,472 | 98.4 |
| Sample #2a | 128,014 | 4,522 | 104.9 |
| Sample #1a | 139,587 | 4,968 | 105.6 |
| Diesel Standard | 92,185 | 2,795 | — |
| Samples Pre-SPE Cleanup | | | |
| Diesel Standard | — | 30,663 | — |
| Sample #5 | — | 25,709 | 83.4 |
| Sample #2 | — | 5,115 | 16.6 |

TABLE 2-continued

| Sample ID | ISTD Response | Fuel Marker Response | Calculated Fuel Marker Concentration (ppb) |
|---|---|---|---|
| Sample #1 | — | 13,292 | 43.1 |
| Diesel Standard | — | 30,994 | — |
| Sample #5 | — | 25,500 | 82.7 |
| Sample #2 | — | 5,090 | 16.5 |
| Sample #1 | — | 13,353 | 43.3 |
| Diesel Standard | — | 30,711 | — |
| Sample #5 | — | 25,389 | 82.3 |
| Sample #2 | — | 5,109 | 16.6 |
| Sample #1 | — | 13,272 | 43.0 |
| Diesel Standard | — | 31,015 | — |

Figure 3A:
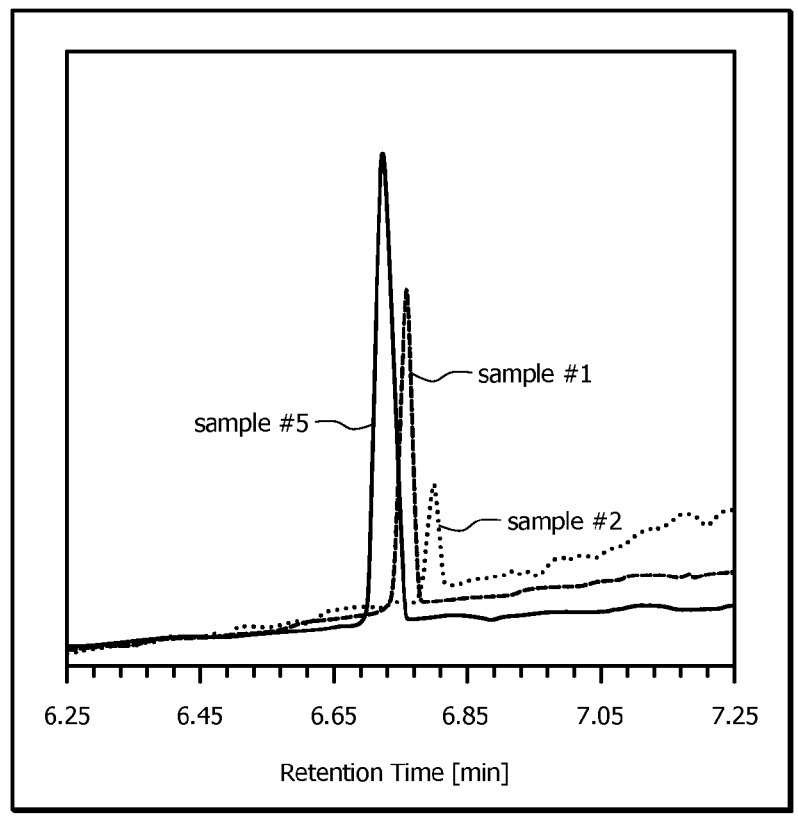
FIG. 3A displays ion chromatograms of a fuel marker in different diesel fuel samples prior to solid phase extraction.
Figure 3B:
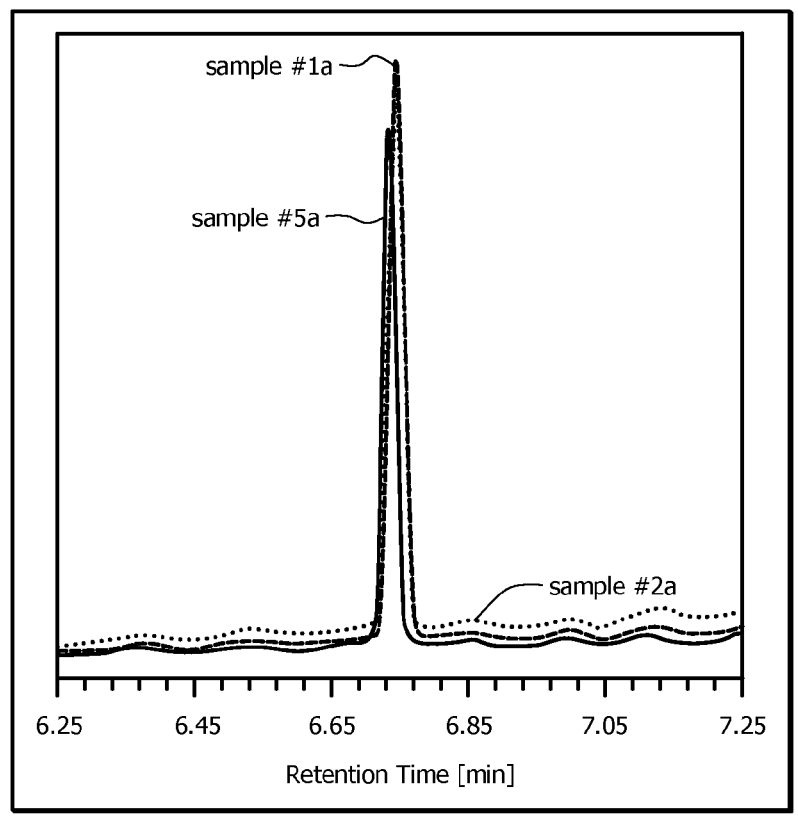
FIG. 3B displays ion chromatograms of a fuel marker in different diesel fuel samples subsequent to solid phase extraction.

FIG. 3A displays extracted ion chromatograms (498.4 m/z) for sample #1, sample #2 and sample #5, prior to SPE. FIG. 3B displays extracted ion chromatograms (498.4 m/z) for sample #1a, sample #2a and sample #5a, subsequent to SPE. As seen from FIG. 3B as compared to FIG. 3A, when the analyzed samples were subjected to SPE, the calculated concentrations were far more accurate. This dramatic increase in accuracy stems from the fact that the interferences present in the diesel samples, which dramatically impact the accurate quantitation of the marker, are removed by the SPE process and hence the responses obtained from the analysis are more consistent across the fuel samples, similarly to the inclusion of the ISTD in the analysis, which provides additional enhanced accuracy to the analysis.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein.

Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first embodiment, which is a method of forming a composition comprising contacting (a) a fuel and (b) at least one compound characterized by Formula I:

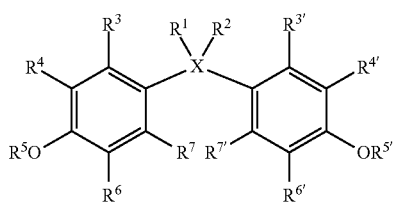

Formula I wherein X can be carbon (C), oxygen (O), or sulfur (S); $R^1$ and $R^2$ can each independently be hydrogen, a $C_1$ to $C_{20}$ alkyl group, or a $C_6$ to $C_{10}$ aryl group; $R^3$ and $R^{3'}$ can each independently be hydrogen or a $C_1$ to $C_4$ alkyl group; $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group; $R^5$ and $R^{5'}$ can each independently be a $C_4$ to $C_{10}$ alkyl group; $R^6$ and $R^{6'}$ can each independently be hydrogen or a $C_1$ to $C_6$ alkyl group; and $R^7$ and $R^{7'}$ can each independently be hydrogen or a $C_1$ to $C_4$ alkyl group; and wherein the compound characterized by Formula I when subjected to gas chromatography-mass spectrometry (GC-MS) using electron ionization produces at least one ion having a mass-to-charge ratio of from about 300 to about 600 at an ionization energy of equal to or greater than about 70 eV.

A second embodiment, which is the method of the first embodiment, wherein X is O or S and $R^1$ and $R^2$ are lone non-bonding electron pairs.

A third embodiment, which is the method of any one of the first and the second embodiments, wherein X is O and wherein the compound characterized by Formula I has Structure A:

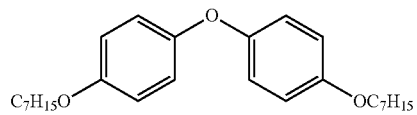

Structure A

A fourth embodiment, which is the method of any one of the first and the second embodiments, wherein X is S and wherein the compound characterized by Formula I has any of Structures B-F:

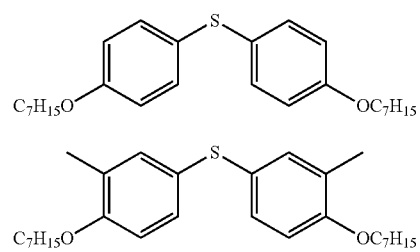

Structure B

Structure C

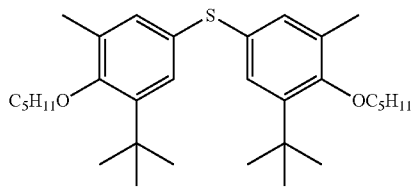

Structure D

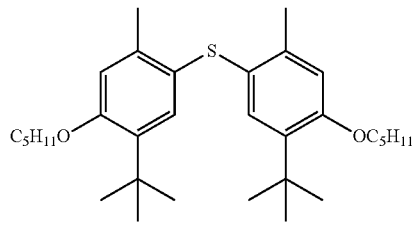

Structure E

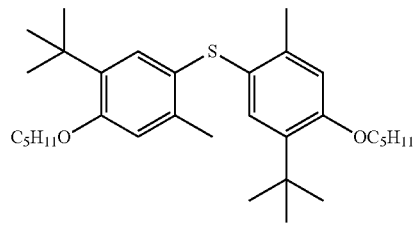

Structure F

A fifth embodiment, which is the method of the first embodiment, wherein X is C and $R^1$ and $R^2$ each independently are selected from the group consisting of a methyl group, an ethyl group, a n-propyl group, an iso-propyl group, a n-butyl group, an iso-butyl group, a sec-butyl group, a tert-butyl group, a pentyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group and a nonadecyl group.

A sixth embodiment, which is the method of the first embodiment, wherein the compound characterized by Formula I has any of Structures G-O:

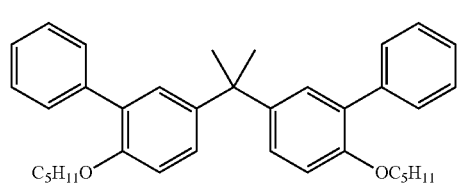

Structure G

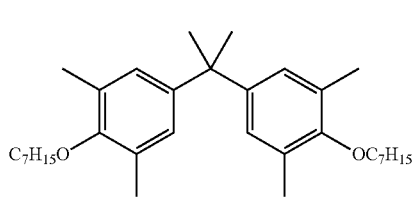

Structure H

-continued

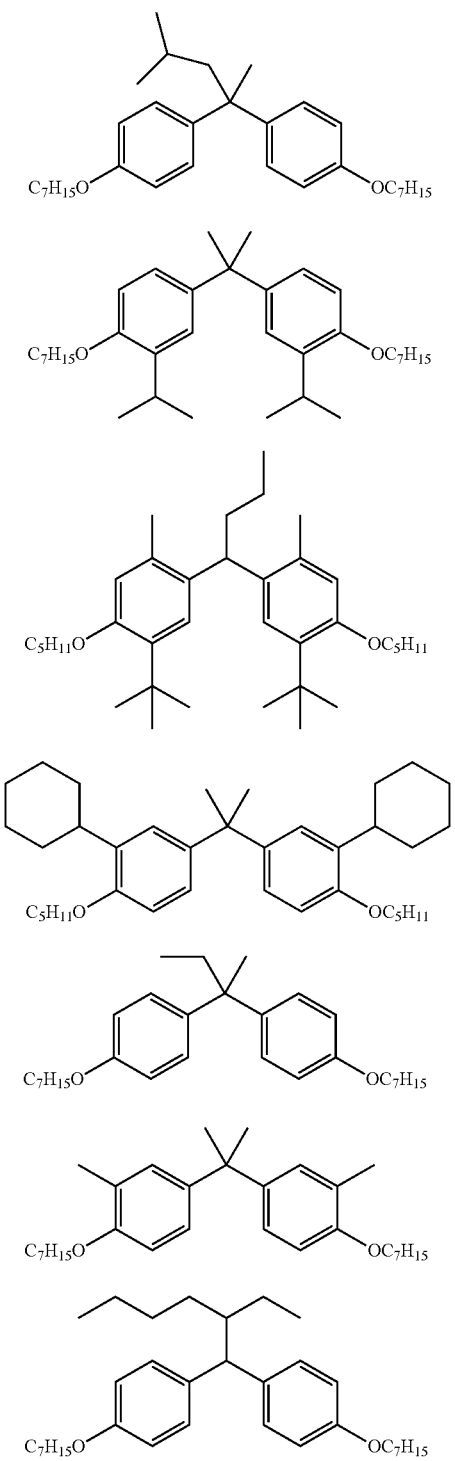

Structure I

Structure J

Structure K

Structure L

Structure M

Structure N

Structure O

A seventh embodiment, which is the method of the first embodiment, wherein X is C and $R^1$ and $R^2$ can each independently be hydrogen, a $C_1$ to $C_{10}$ alkyl group, or a $C_6$ to $C_{10}$ aryl group.

An eighth embodiment, which is the method of the seventh embodiment, wherein the $C_6$ to $C_{10}$ aryl group is phenyl, a substituted phenyl, tolyl, a substituted tolyl, xylyl or a substituted xylyl.

A ninth embodiment, which is the method of any one of the seventh and the eighth embodiments, wherein the compound characterized by Formula I has Structure P:

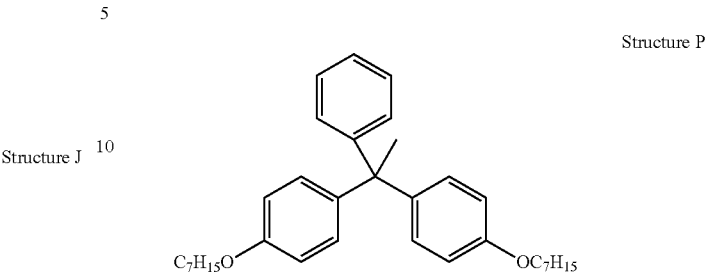

Structure P

A tenth embodiment, which is the method of the first embodiment, wherein X is C and $R^3$ and $R^{3'}$ can each independently be a methyl group or hydrogen.

An eleventh embodiment, which is the method of the first embodiment, wherein X is C and $R^4$, $R^{4'}$, $R^5$, and $R^{5'}$ can each independently be a $C_1$ to $C_{10}$ alkyl group, a $C_4$ to $C_{10}$ cycloalkyl group, or a $C_6$ to $C_{10}$ aryl group.

A twelfth embodiment, which is the method of the eleventh embodiment, wherein $R^5$ and $R^{5'}$ are both a pentyl group or a heptyl group.

A thirteenth embodiment, which is the method of any one of the eleventh and the twelfth embodiments, wherein the $C_4$ to $C_{10}$ cycloalkyl group is a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group.

A fourteenth embodiment, which is the method of the first embodiment, wherein X is C, $R^1$ and $R^2$ are a methyl group, and $R^5$ and $R^{5'}$ are both a $C_4$ to $C_{10}$ alkyl group.

A fifteenth embodiment, which is the method of any one of the first through the fourteenth embodiments, wherein the fuel comprises gasoline, diesel, jet fuel, kerosene, non-petroleum derived fuels, alcohol fuels, ethanol, methanol, propanol, butanol, biodiesel, maritime fuels, or combinations thereof.

A sixteenth embodiment, which is the method of any one of the first through the fifteenth embodiments, wherein the compound characterized by Formula I is present in the composition in an amount of from about 1 ppb to about 50 ppm, based on the total weight of the composition.

A seventeenth embodiment, which is the method of any one of the first through the sixteenth embodiments, wherein the composition comprises at least 2 compounds characterized by Formula I.

An eighteenth embodiment, which is the method of the seventeenth embodiment further comprising (i) acquiring a fuel sample; (ii) subjecting the fuel sample to GC-MS to yield GC-MS data; and (iii) comparing the GC-MS data of the fuel sample with the GC-MS data of the composition.

A nineteenth embodiment, which is the method of the eighteenth embodiment further comprising determining an amount of the compound characterized by Formula I present in the composition and the fuel sample based on the GC-MS data.

A twentieth embodiment, which is the method of any one of the first through the nineteenth embodiments further comprising subjecting the composition to surface enhanced Raman scattering spectroscopy.

A twenty-first embodiment, which is the method of any one of the first through the twentieth embodiments further comprising subjecting the composition to nuclear magnetic resonance spectroscopy.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of forming a composition comprising contacting (a) a fuel and (b) at least one compound characterized by Formula I:

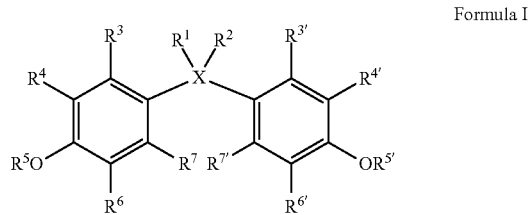

Formula I wherein X can be carbon (C), oxygen (O), or sulfur (S); wherein, when X is C, $R^1$ and $R^2$ can each independently be hydrogen, a $C_1$ to $C_{20}$ alkyl group, or a $C_6$ to $C_{10}$ aryl group, and wherein the $C_6$ to $C_{10}$ aryl group is a hydrocarbon; wherein, when X is O or S, $R^1$ and $R^2$ are lone non-bonding electron pairs; $R^3$ and $R^{3'}$ can each independently be hydrogen or a $C_1$ to $C_4$ alkyl group; $R^4$ and $R^{4'}$ can each independently be hydrogen, a $C_1$ to $C_4$ alkyl group, a $C_4$ to $C_{10}$ cycloalkyl group, or a $C_6$ to $C_{10}$ aryl group; $R^5$ and $R^{5'}$ can each independently be a $C_4$ to $C_{10}$ alkyl group; $R^6$ and $R^{6'}$ can each independently be hydrogen or a $C_1$ to $C_6$ alkyl group; and $R^7$ and $R^{7'}$ can each independently be hydrogen or a $C_1$ to $C_4$ alkyl group;

and wherein the compound characterized by Formula I when subjected to gas chromatography—mass spectrometry (GC-MS) using electron ionization produces at least one ion having a mass-to-charge ratio of from about 300 to about 600 at an ionization energy of equal to or greater than about 70 eV.

2. The method of claim 1 wherein X is O and wherein the compound characterized by Formula I has Structure A:

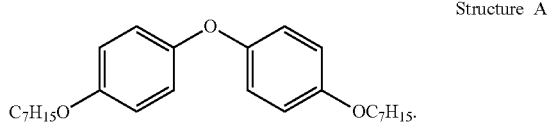

Structure A

3. The method of claim 1 wherein X is S and wherein the compound characterized by Formula I has any of Structures B-F:

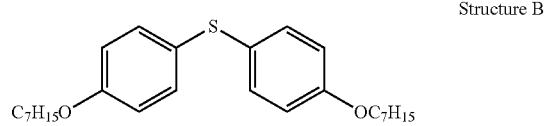

Structure B

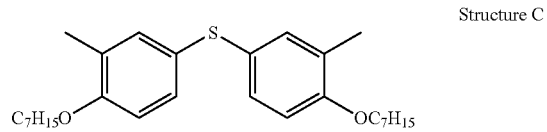

Structure C

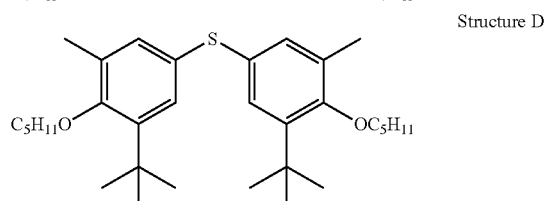

Structure D

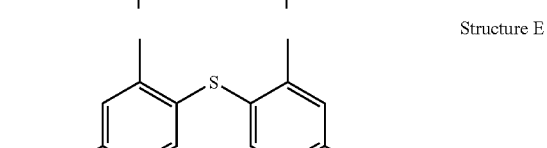

Structure E

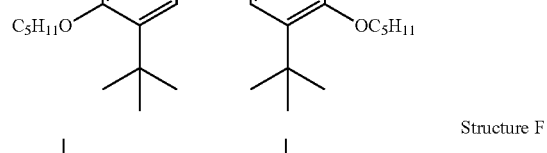

Structure F

4. The method of claim 1 wherein X is C and $R^1$ and $R^2$ each independently are selected from the group consisting of a methyl group, an ethyl group, a n-propyl group, an iso-propyl group, a n-butyl group, an iso-butyl group, a sec-butyl group, a tort-butyl group, a pentyl group, a n-pentyl group, an iso-pentyl group, a sec-pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group and a nonadecyl group.

5. The method of claim 1 wherein the compound characterized by Formula I has any of Structures G-O:

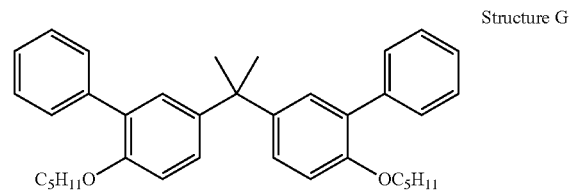

Structure G

-continued

Structure H
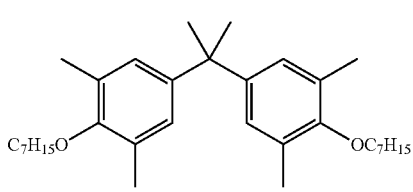

Structure I
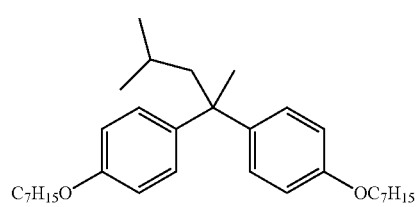

Structure J
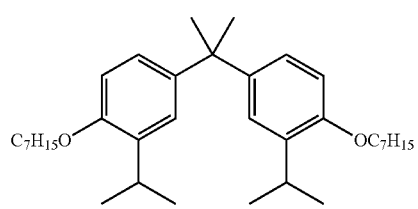

Structure K
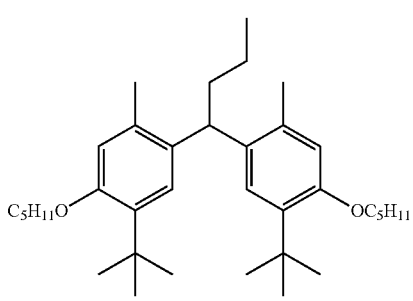

Structure L
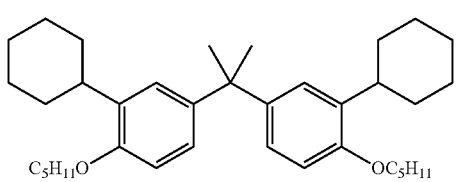

Structure M
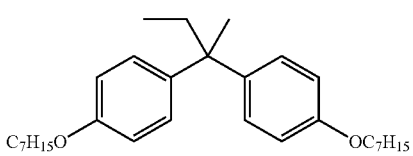

Structure N
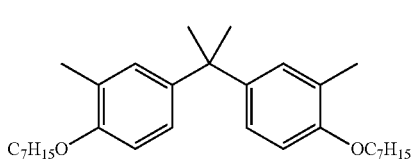

Structure O
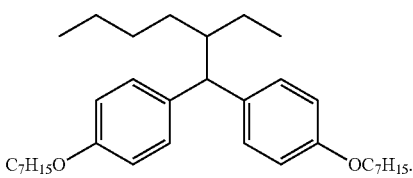

6. The method of claim 1 wherein X is C and $R^1$ and $R^2$ can each independently be hydrogen, a $C_1$ to $C_{10}$ alkyl group, or a $C_6$ to $C_{10}$ aryl group.

7. The method of claim 6 wherein the $C_6$ to $C_{10}$ aryl group is phenyl, a substituted phenyl, tolyl, a substituted tolyl, xylyl or a substituted xylyl.

8. The method of claim 6 wherein the compound characterized by Formula I has Structure P:

Structure P
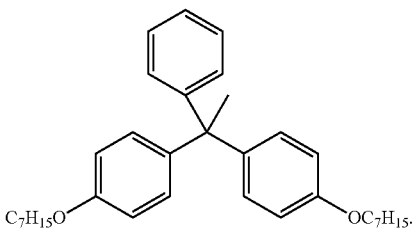

9. The method of claim 1 wherein X is C and $R^3$ and $R^{3'}$ can each independently be a methyl group or hydrogen.

10. The method of claim 1 wherein X is C and $R^4$, and $R^{4'}$ can each independently be a $C_1$ to $C_{10}$ alkyl group, a $C_4$ to $C_{10}$ cycloalkyl group, or a $C_6$ to $C_{10}$ aryl group.

11. The method of claim 10 wherein $R^5$ and $R^{5'}$ are both a pentyl group or a heptyl group.

12. The method of claim 10 wherein the $C_4$ to $C_{10}$ cycloalkyl group is a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group.

13. The method of claim 1 wherein X is C, $R^1$ and $R^2$ are a methyl group, and $R^5$ and $R^{5'}$ are both a $C_4$ to $C_{10}$ alkyl group.

14. The method of claim 1 wherein the fuel comprises gasoline, diesel, jet fuel, kerosene, non-petroleum derived fuels, alcohol fuels, ethanol, methanol, propanol, butanol, biodiesel, maritime fuels, or combinations thereof.

15. The method of claim 1 wherein the compound characterized by Formula I is present in the composition in an amount of from about 1 ppb to about 50 ppm, based on the total weight of the composition.

16. The method of claim 1 wherein the composition comprises at least 2 compounds characterized by Formula I.

17. The method of claim 16 further comprising (i) acquiring a fuel sample; (ii) subjecting the fuel sample to GC-MS to yield GC-MS data; and (iii) comparing the GC-MS data of the fuel sample with the GC-MS data of the composition.

18. The method of claim 17 further comprising determining an amount of the compound characterized by Formula I present in the composition and the fuel sample based on the GC-MS data.

19. The method of claim 1 further comprising subjecting the composition to surface enhanced Raman scattering spectroscopy.

20. The method of claim 1 further comprising subjecting the composition to nuclear magnetic resonance spectroscopy.

21. The method of claim 1 wherein $R^3$ and $R^{3'}$ are hydrogen.

* * * * *